(12) United States Patent
Wei

(10) Patent No.: US 8,335,560 B2
(45) Date of Patent: Dec. 18, 2012

(54) DERIVED ELECTROCARDIOGRAM GENERATING SYSTEM AND DERIVED ELECTROCARDIOGRAM GENERATING METHOD

(75) Inventor: Daming Wei, Fukushima (JP)

(73) Assignees: Wei Daming, Fukushima (JP); Nihon Kohden Corporation, Tokyo (JP)

( * ) Notice: Subject to any disclaimer, the term of this patent is extended or adjusted under 35 U.S.C. 154(b) by 0 days.

(21) Appl. No.: 13/194,014

(22) Filed: Jul. 29, 2011

(65) Prior Publication Data

US 2012/0029371 A1 Feb. 2, 2012

(30) Foreign Application Priority Data

Jul. 30, 2010 (JP) .................. 2010-172483

(51) Int. Cl.
*A61B 5/04* (2006.01)
(52) U.S. Cl. ...................................................... 600/509
(58) Field of Classification Search .................. 600/509
See application file for complete search history.

(56) References Cited

U.S. PATENT DOCUMENTS

| 7,623,910 B2 * | 11/2009 | Couderc et al. ............. 600/509 |
| 2002/0035334 A1 | 3/2002 | Meij et al. |
| 2002/0045837 A1 | 4/2002 | Wei et al. |
| 2002/0087088 A1 | 7/2002 | Brodnick |
| 2004/0015089 A1 | 1/2004 | Brodnick |
| 2006/0224071 A1 | 10/2006 | Stewart |
| 2006/0235317 A1 | 10/2006 | Wei |
| 2011/0288425 A1 | 11/2011 | Stewart |

FOREIGN PATENT DOCUMENTS

| EP | 1221299 A2 | 7/2002 |
| EP | 1618841 A1 | 1/2006 |
| JP | 2002-034943 A | 2/2002 |
| JP | 4153950 B2 | 9/2008 |
| WO | 0211615 A2 | 2/2002 |
| WO | 2005011492 A2 | 2/2005 |

OTHER PUBLICATIONS

Extended European Search Report dated Sep. 6, 2012, issued by the European Patent Office in counterpart Application No. 11176067.4.

* cited by examiner

*Primary Examiner* — George Manuel
(74) *Attorney, Agent, or Firm* — Sughrue Mion, PLLC

(57) ABSTRACT

A derived electrocardiogram generating system includes: a personal coefficient database which stores personal coefficients specific to a subject, the personal coefficients being acquired from the subject; a population coefficient database which stores population coefficients which are average values of conversion coefficients acquired from an unspecified large number of persons belonging to a statistically significant population; and an electrocardiograph control portion: which generates a derived electrocardiogram of the subject using the personal coefficients when the personal coefficients are present in the personal coefficient database; and which generates a derived electrocardiogram of the subject using the population coefficients when the personal coefficients are absent in the personal coefficient database.

12 Claims, 15 Drawing Sheets

DERIVED ELECTROCARDIOGRAM GENERATING SYSTEM AND DERIVED ELECTROCARDIOGRAM GENERATING METHOD

BACKGROUND OF THE INVENTION

The present invention relates to a derived electrocardiogram generating system and a derived electrocardiogram generating method which can improve accuracy in diagnosis of heart disease of a subject even with a small number of electrocardiographically measuring electrodes so as to achieve higher derivation accuracy than any existing technique.

To acquire a standard 12-lead electrocardiogram of a patient, 10 electrodes connected to an electrocardiograph are used so as to be mounted at six places for measuring chest leads and at four places for measuring limb leads respectively. Based on electrocardiographic potentials detected from the 10 electrodes, six limb lead waveforms (I, II, III, aVR, aVL and aVF) of standard 12-lead waveforms and six chest lead waveforms (V1, V2, V3, V4, V5 and V6) of the standard 12-lead waveforms are calculated and outputted by the electrocardiograph.

The following relations are established between lead waveforms for obtaining a standard 12-lead electrocardiogram and electrocardiographic potentials in measurement portions.

I lead: vL−vR
II lead: vF−vR
III lead: vF−vL
aVR lead: vR−(vL+vF)/2
aVL lead: vL−(vR+vF)/2
aVF lead: vF−(vL+vR)/2
V1 lead: v1−(vR+vL+vF)/3
V2 lead: v2−(vR+vL+vF)/3
V3 lead: v3−(vR+vL+vF)/3
V4 lead: v4−(vR+vL+vF)/3
V5 lead: v5−(vR+vL+vF)/3
V6 lead: v6−(vR+vL+vF)/3 where each sign $\underline{v}$ represents a potential detected in each electrode mounting position.

When heart disease of a patient is diagnosed with a large number of electrodes in this manner in a fully-equipped hospital or the like, the diagnosis can be performed in the condition that the patient is kept quiet in bed.

However, for example, in the case of home care or emergent care, it is often difficult to use a large number of electrodes and mount the electrodes in proper positions on a body surface of a living body respectively, in view of patient's condition. Further, it may be also difficult to transmit multichannel signals in order to obtain a large number of lead waveforms. In such a case, there is only one channel (one lead) where a signal of an electrocardiogram can be transmitted. Thus, some lead waveforms of standard 12-lead waveforms are measured with no more than 2 to 4 electrodes, so as to diagnose heart disease.

From this view point, the present inventor has developed a derived 12-lead electrocardiogram constructing system and an electrocardiographic inspection apparatus for reconstructing a standard 12-lead electrocardiogram with which various heart diseases can be diagnosed and treated properly, by use of a lead system subset consisting of a minimum number of leads for obtaining a related-art standard 12-lead electrocardiogram (see JP-A-2002-34943, particularly paragraphs 0020-0033).

That is, in the system for constructing a derived 12-lead electrocardiogram as disclosed in JP-A-2002-34943, limb leads I and II and two chest leads V1 and V5 or V6 for obtaining the standard 12-lead electrocardiogram are used as a lead system subset consisting of a minimum number of channels. From these leads, leads III and aVs (aVR, aVL and aVF) are arithmetically obtained based on the aforementioned specific relations of the respective leads. In addition, the other chest leads V2, V3, V4 and V6 or V5 are arithmetically derived using conversion coefficients (deriving matrix) created in consideration of relationship among potentials, lead vectors and cardiac vectors.

Since a related-art lead system subset of a standard 12-lead electrocardiogram is used, a derived 12-lead electrocardiogram is obtained thus from the specific relations of the respective leads and the created conversion coefficients. Thus, electrodes can be easily and surely positioned in predetermined portions respectively when the electrodes are attached thereto. This work does not require much skill. In addition, a high-accuracy standard 12-lead electrocardiogram can be reconstructed. Thus, various heart diseases can be diagnosed and treated properly.

Accordingly, the related-art electrocardiograph can check and diagnose abnormality in electrocardiographic waveforms not only when a standard 12-lead electrocardiogram is obtained from six limb leads and six chest leads using ten electrodes but also when a high-accuracy derived 12-lead electrocardiogram is derived by the system disclosed in JP-A-2002-34943.

Another case where a derived electrocardiogram is required with respect to standard 12-lead applications will be described. With the aforementioned standard 12-lead electrocardiogram, which is applied to diagnosis of myocardial infarction, abnormality in electrocardiographic waveforms can be checked and diagnosed easily about an anterior wall or a side wall where a coronary artery providing a blood flow for a cardiac muscle is occluded. However, sensitivity deteriorates about a posterior wall or a right posterior wall where an electrode is attached in a farther position from the heart. According to research paper, ST increase of acute myocardial infarction (AMI) in many posterior walls appears in the leads V7, V8 and V9. Thus, ST increase may be often overlooked in a standard 12-lead electrocardiogram. It has been therefore proposed to measure the aforementioned additional leads if necessary. However, measurement must be carried out twice when a standard electrocardiograph is used. In addition, it is difficult to measure the leads V7, V8 and V9 because the leads V7, V8 and V9 are located on the back. Thus, the present inventor has proposed an electrocardiograph with an additional lead function and an additional lead electrocardiogram deriving method in which electrocardiographic waveforms V7, V8 and V9 for diagnosis of inferior infarction and electrocardiographic waveforms V3R, V4R and V5R for diagnosis of right ventricle infarction are derived from measured signals of a standard 12-lead electrocardiogram so that high-accuracy diagnosis information can be provided (see Japanese Patent No. 4153950).

According to the related-art electrocardiogram deriving method (e.g. Japanese Patent No. 4153950), electrocardiographic waveforms in portions to which electrodes are not attached, that is, derived electrocardiographic waveforms are derived using conversion coefficients. Therefore, the accuracy of the conversion coefficients gives influence to the derived electrocardiograph of the subject and the diagnostic accuracy of heart diseases. Average values of conversion coefficients (hereinafter referred to as population coefficient) acquired from an unspecified large number of persons are used as conversion coefficients. The population coefficients can guarantee some conversion accuracy statistically but cannot be regarded as optimum conversion coefficients for an individual subject. For this reason, there may occur a clinically unsatisfied difference between the derived electrocardiogram and its "true values" (values which would be obtained if they were measured).

On the other hand, it can be also considered that electrocardiographic waveforms of non-measurement portions are derived using conversion coefficients which can be applied only to a specific subject (hereinafter referred to as personal coefficients). However, there has been no specific proposal or technique like that so far.

Most of derived electrocardiograms which have been proposed so far are 12-lead electrocardiograms. In order to improve the diagnostic accuracy of heart disease of a subject who has a unique heart disease, a large number of coefficients (population or personal coefficients) which can generate a derived electrocardiogram of portions effective in the diagnosis of the unique heart disease of the subject must be prepared. However, there has been no proposal or technique for such a large number of coefficients.

Further, though it is understood to use personal coefficients specific to a subject, there has been no proposal for solving some technical themes such as how to acquire the personal coefficients, how to use the personal coefficients, and how to solve the problem that the personal coefficients of the specific subject cannot be used when the personal coefficients are absent in an electrocardiograph which is in use.

SUMMARY

It is therefore an object of the invention to provide a derived electrocardiogram generating system and a derived electrocardiogram generating method which can improve accuracy in diagnosis of heart disease of a subject even with a small number of electrocardiographically measuring electrodes In order to achieve the object, according to the invention, there is provided a derived electrocardiogram generating system comprising: a personal coefficient database which stores personal coefficients specific to a subject, the personal coefficients being acquired from the subject; a population coefficient database which stores population coefficients which are average values of conversion coefficients acquired from an unspecified large number of persons belonging to a statistically significant population; and an electrocardiograph control portion: which generates a derived electrocardiogram of the subject using the personal coefficients when the personal coefficients are present in the personal coefficient database; and which generates a derived electrocardiogram of the subject using the population coefficients when the personal coefficients are absent in the personal coefficient database.

The derived electrocardiogram generating system may further include a plurality of electrocardiographically measuring electrodes which are adapted to be attached to desired measurement portions of a body surface of the subject to acquire electrocardiographic signals. The electrocardiograph control portion may calculate the personal coefficients of the subject from the acquired electrocardiographic signals, and store the calculated personal coefficients in the personal coefficient database.

The personal coefficients of the subject may be stored in the personal coefficient database on a basis of each derived electrocardiogram type.

The electrocardiograph control portion may display a message prompting creation of the personal coefficients when the personal coefficients of the subject are absent in the personal coefficient database.

The derived electrocardiogram generating system may further include: an electrocardiograph which generates the derived electrocardiogram of the subject; and an electrocardiogram management system which manages information about the derived electrocardiogram held by the electrocardiograph. The personal coefficient database may be disposed in each of the electrocardiograph and the electrocardiogram management system, and the population coefficient database and the electrocardiograph control portion may be disposed in the electrocardiograph.

The derived electrocardiogram generating system may further include: a plurality of electrocardiogram management apparatuses each of which includes the electrocardiograph and the electrocardiogram management system, the plurality of electrocardiogram management apparatuses being connected to one another through a connection network.

The plurality of electrocardiogram management apparatuses may include different kinds of electrocardiogram management apparatus, and the electrocardiogram control portion of the electrocardiograph included in one kind of electrocardiogram management apparatus may acquire the personal coefficients of the subject from one of the personal coefficient database of the electrocardiograph included in this kind of electrocardiogram management apparatus, the personal coefficient database of the electrocardiogram management system included in this kind of electrocardiogram management apparatus, and the personal coefficient database of the electrocardiogram management system included in another kind of electrocardiogram management apparatus.

The electrocardiogram control portion of the electrocardiograph included in one kind of electrocardiogram management apparatus may retrieve the personal coefficients in turn from the personal coefficient database of the electrocardiograph included in this kind of electrocardiogram management apparatus, the personal coefficient database of the electrocardiogram management system included in this kind of electrocardiogram management apparatus, and the personal coefficient database of the electrocardiogram management system included in another kin of electrocardiogram management apparatus.

The personal coefficients may be stored in time series on a basis of each electrocardiogram type and each subject.

The population coefficients may be stored on a basis of each sex, each age, and each electrocardiogram type.

According to the invention, there is also provided a derived electrocardiogram generating method in a derived electrocardiogram generating system including a personal coefficient database and a population coefficient database, the personal coefficient database storing personal coefficients acquired from a subject, the population coefficient database storing population coefficients which are average values of conversion coefficients acquired from an unspecified large number of persons belonging to a statistically significant population, the method comprising: determining whether the personal coefficients are present in the personal coefficient database or not; acquiring the personal coefficients when the personal coefficients are present in the personal coefficient database, and acquiring the population coefficients from the population coefficient database when the personal coefficients are absent in the personal coefficient database; and generating a derived electrocardiogram of the subject using the acquired personal coefficients or the acquired population coefficients.

The derived electrocardiogram generating method may further include: attaching a plurality of electrocardiographically measuring electrodes to desired measurement portions of a body surface of the subject to acquire electrocardiographic signals when the personal coefficients of the subject are absent in the personal coefficient database; calculating the personal coefficients of the subject from the acquired electrocardiographic signals; and storing the calculated personal coefficients in the personal coefficient database.

DETAILED DESCRIPTION OF EMBODIMENTS

Figure 1:
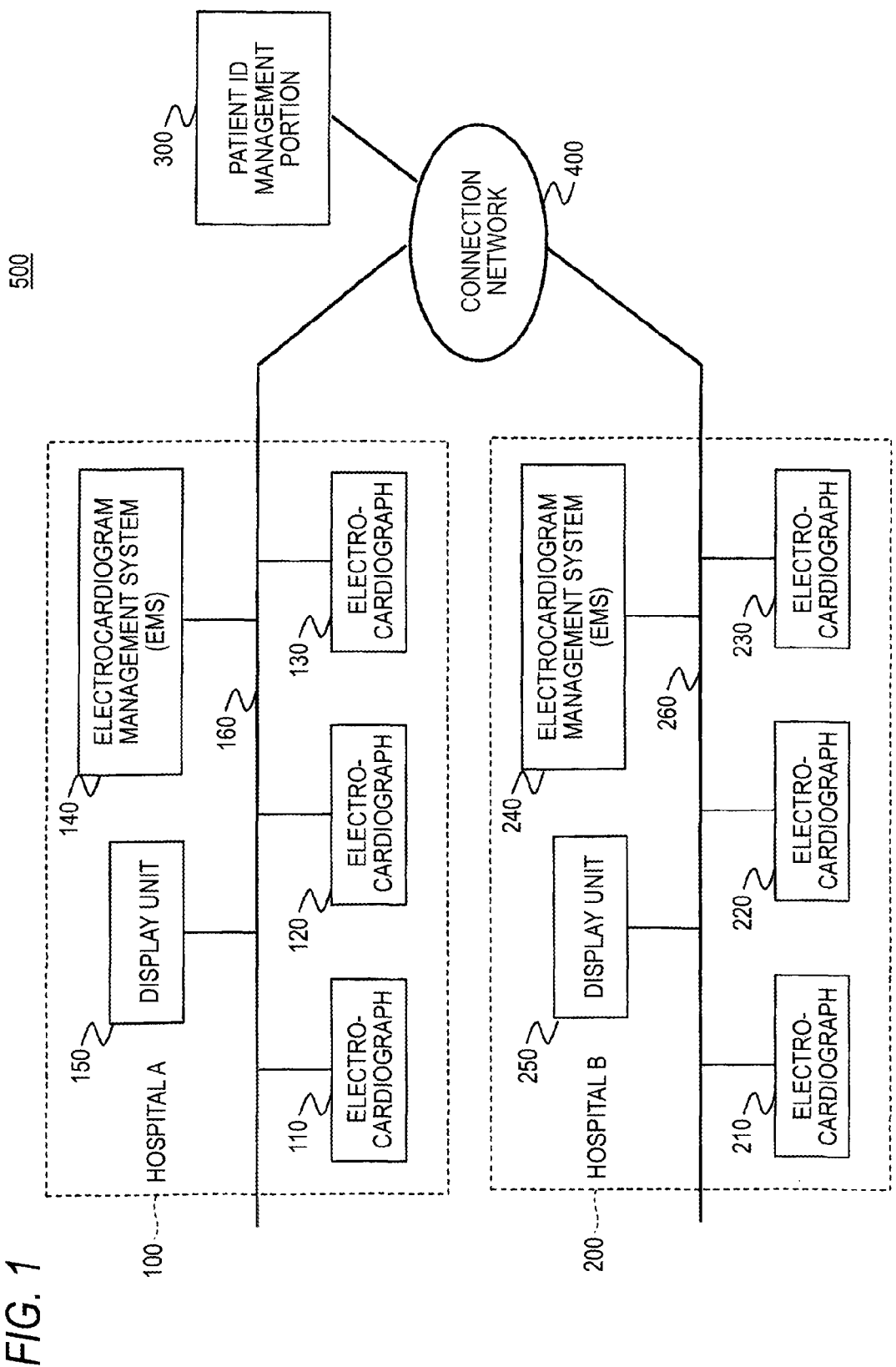
FIG. 1 is a block diagram of a derived electrocardiogram generating system according to an embodiment of the invention.

An embodiment of the invention will be described below in detail with reference to the drawings. In this embodiment, the term "patients" will be used as a specific example of subjects. The subjects may include not only patients who receive examinations in hospitals but also persons who use other places than hospitals, such as health screening centers, clinics, ordinary homes, etc. where the persons receive health examinations.

It is a matter of course that a derived electrocardiogram generating system and a derived electrocardiogram generating method according to the embodiment can be applied to 18 types (type A to type R) of derived electrocardiograms described below. In addition to the 18 derived electrocardiogram types, the derived electrocardiogram generating system and the derived electrocardiogram generating method according to the embodiment can be also applied to derived electrocardiogram types specific to patients (custom-made derived electrocardiogram types), which can generate derived electrocardiograms of desired portions effective in diagnosing heart diseases of the patients.

The following derived 12-lead electrocardiograms and derived additional-lead electrocardiograms (18-lead electrocardiograms) are of related-art derived electrocardiogram types.

The following derived additional-lead electrocardiograms (derived electrocardiograms for Brugada syndrome diagnosis) and derived mapping electrocardiogram (160-lead mapping electrocardiogram) are of derived electrocardiogram types which have not been known and have not been generally used yet.

The reference signs V1+, V2+, V1++ and V2++ in the derived additional-lead electrocardiograms (derived electrocardiograms for Brugada syndrome diagnosis) represent portions effective in diagnosing heart diseases of patients. The portion V1+ is a portion on a first rib of a lead V1; V2+ is a portion on the first rib of a lead V2; V1++ is a portion on a second rib of the lead V1; and V2++ is a portion on the second rib of the lead V2. Derived electrocardiograms of the portions V1+, V2+, V1++ and V2++ are obtained to improve the diagnostic accuracy of a heart disease called Brugada syndrome.

The derived mapping electrocardiogram (160-lead mapping electrocardiogram) generates electrocardiograms in 160 places on a body surface of a patient. The derived mapping electrocardiogram (160-lead mapping electrocardiogram) can obtain a derived electrocardiogram in a desired portion easily. Thus, any heart disease of a patient can be diagnosed with high accuracy even if the patient has a unique heart.

A. Derived 12-Lead Electrocardiograms
(1) V1, V3, V5 and V6 derived from four leads I, II, V2 and V4 (type A)
(2) V2, V3, V5 and V6 derived from four leads I, II, V1 and V4 (type B)
(3) V1, V3, V4 and V6 derived from four leads I, II, V2 and V5 (type C)
(4) V2, V3, V4 and V6 derived from four leads I, II, V1 and V5 (type D)
(5) V1, V3, V4 and V5 derived from four leads I, II, V2 and V6 (type E)
(6) V2, V3, V4 and V5 derived from four leads I, II, V1 and V6 (type F)

B. Derived Additional-Lead Electrocardiograms (18-Lead Electrocardiograms)
(7) V7, V8, V9, V3R, V4R and V5R derived from 12 leads and V1-V6 (type G)
(8) V7, V8, V9, V3R, V4R, V5R and V6R derived from 12 leads I, II, and V1-V6 (type H)
(9) V7, V8, V9, V3R, V4R, V5R and V6R derived from 4 leads I, II, V1 and V4 (type I)
(10) V7, V8, V9, V3R, V4R, V5R and V6R derived from 4 leads I, II, V2 and V5 (type J)
(11) V7, V8, V9, V3R, V4R, V5R and V6R derived from 4 leads I, II, V1 and V5 (type K)
(12) V7, V8, V9, V3R, V4R, V5R and V6R derived from 4 leads I, II, V2 and V6 (type L)

C. Derived Additional-Lead Electrocardiograms (Derived Lead Electrocardiograms for Brugada Syndrome Diagnosis)
(13) V1+, V2+, V1++ and V2++ derived from 12 leads I, and V1-V6 (type M)
(14) V1+, V2+, V1++ and V2++ derived from 4 leads I, II, V1 and V4 (type N)
(15) V1+, V2+, V1++ and V2++ derived from 4 leads I, II, V2 and V5 (type O)
(16) V1+, V2+, V1++ and V2++ derived from 4 leads I, II, V1 and V5 (type B)

(17) V1+, V2+, V1++ and V2++ derived from 4 leads I, II, V2 and V6 (type Q)

D. Derived Mapping Electrocardiogram (160-Lead Mapping Electrocardiogram)

(18) body-surface 8×20 potential mapping derived from 12 leads I, II and V1-V6 (type R)

The derived electrocardiogram generating system according to the embodiment has a database which stores population coefficients corresponding to the aforementioned twelve derived electrocardiogram types (derived 12-lead electrocardiograms and derived additional-lead electrocardiograms (18-lead electrocardiograms)) which are normally used. In addition, the derived electrocardiogram generating system according to the embodiment has a database which stores personal coefficients corresponding to all the aforementioned eighteen derived electrocardiogram types and corresponding to custom-made derived electrocardiogram types other than the eighteen derived electrocardiogram types.

A derived electrocardiogram can be generated using population coefficients or personal coefficients based on the following principle. The principle will be described with a derived 12-lead electrocardiogram of the aforementioned type C by way of example.

To generate a derived 12-lead electrocardiogram of the type C, a total of six electrocardiographically measuring electrodes are attached to a body surface of a patient. The electrocardiographically measuring electrodes are positioned in four places of left and right arm portions (electrodes L and R) and left and right lower limbs (electrodes LL and RL) for detecting electrocardiographic signals of leads I and II and two places where a fourth intercostal space at a left sternal border and a left anterior axillary line intersect with a horizontal line crossing a fifth intercostal space for detecting electrocardiographic signals of two chest leads (V2 and V5).

From the electrocardiographic signals corresponding to the four leads including the leads I and II and the two chest leads (V2 and V5) detected by the electrocardiographically measuring electrodes, a derived electrocardiogram including the other four chest leads V1, V3, V4 and V6 which have not been measured actually by the electrocardiographically measuring electrodes is generated using the personal coefficients or the population coefficients.

The derived electrocardiogram including the chest leads V1, V3, V4 and V6 (derived lead vectors) can be obtained by substituting the personal or population coefficients and the electrocardiographic signals (measured lead vectors) corresponding to the four leads including the leads I and II and the two chest leads (lead V2 and lead V5) into the following determinant and expanding the determinant.

$$\begin{bmatrix} V1 \\ V3 \\ V4 \\ V6 \end{bmatrix} = \begin{bmatrix} T1I & T1II & T12 & T15 \\ T3I & T3II & T32 & T35 \\ T41 & T4II & T42 & T45 \\ T6I & T6II & T62 & T65 \end{bmatrix} \begin{bmatrix} VI \\ VII \\ V2 \\ V5 \end{bmatrix}$$

For the derived 12-lead electrocardiogram of the type C, the personal coefficients or the population coefficients are obtained in the following procedure.

To obtain personal coefficients of a patient, electrocardiographically measuring electrodes are attached to 10 places on a body surface of the patient. The places where the electrodes are attached correspond to portions where the electrodes can detect ten electrocardiographic signals of leads I, II, V1, V2, V3, V4, V5 and V6. The leads V1, V3, V4 and V6 as derived lead vectors and the leads I, II, V2 and V5 as measured lead vectors can be measured actually from the ten electrocardiographically measuring electrodes. When these leads are substituted into the aforementioned determinant, personal coefficients (T1I, T1II, T12, T15, T3I, T3II, T32, T35, T4I, T4II, T42, T45, T6I, T6II, T62 and T65) of the patient can be obtained by a least square method. The personal coefficients are stored in a database of the derived electrocardiogram generating system in time series on a basis of each patient and each derived electrocardiogram type.

To obtain population coefficients, average values of a plurality of conversion coefficients (T1I, T1II, T12, T15, T3I, T3II, T32, T35, T4I, T4II, T42, T45, T6I, T6II, T62 and T65) acquired in the aforementioned manner from an unspecified large number of persons belonging to a statistically significant population are obtained. The population coefficients are obtained on a basis of each sex and each age and stored in a database of the derived electrocardiogram generating system on a basis of each sex, each age and each derived electrocardiogram type.

To obtain a derived electrocardiogram of desired portions effective in diagnosing heart disease of a patient who has a unique heart, electrocardiographically measuring electrodes are attached to portions selected as the most effective in diagnosing the heart disease. Personal coefficients are obtained using the aforementioned principle and stored in a database. When electrocardiographic measurement on the patient is carried out using the personal coefficients, a custom-made derived electrocardiogram effective in diagnosing the heart disease of the patient can be obtained with high accuracy.

In this manner, personal coefficients required for generating a derived electrocardiogram of a specific patient can be created in the derived electrocardiogram generating system and the derived electrocardiogram generating method according to the embodiment. When a derived electrocardiogram is generated using the created personal coefficients, the diagnostic accuracy of heart disease of the patient can be improved.

Next, description will be made on the configuration of the derived electrocardiogram generating system according to the embodiment.

FIG. 1 is a block diagram of the derived electrocardiogram generating system according to the embodiment.

A derived electrocardiogram generating system 500 has an electrocardiogram management apparatus 100 installed by a hospital A, an electrocardiogram management apparatus 200 installed by a hospital B, a patient ID management portion 300 for managing patient IDs (unique IDs and individual IDs) of the hospitals A and B, and a connection network 400. The electrocardiogram management apparatuses 100 and 200 and the patient ID management portion 300 are connected to one another through the connection network 400.

This embodiment shows the case where the electrocardiogram management apparatuses 100 and 200 are installed in hospitals, by way of example. The electrocardiogram management apparatuses 100 and 200 do not have to be installed in hospitals but may be provided in facilities other than hospitals, such as health screening centers, clinics, schools, geriatric facilities, etc. where health examinations may be carried out. The patient ID management portion 300 is installed outside the electrocardiogram management apparatuses 100 and 200. However, the patient ID management portion 300 may be disposed, for example, in the electrocardiogram management apparatus 100 of the hospital A. The connection network 400 may be a private line connecting the electrocardiogram management apparatuses 100 and 200 with the patient ID management portion 300 or may be a wire or wireless Internet line with security measures.

The electrocardiogram management apparatus 100 of the hospital A has electrocardiographs 110, 120 and 130, an electrocardiogram management system (EMS) 140 and a display unit 150. The electrocardiographs 110, 120 and 130, the electrocardiogram management system (EMS) 140 and the display unit 150 are connected to one another through an intrahospital network 160. The electrocardiogram management apparatus 200 of the hospital B has electrocardiographs 210, 220 and 230, an electrocardiogram management system (EMS) 240 and a display unit 250. The electrocardiographs 210, 220 and 230, the electrocardiogram management system (EMS) 240 and the display unit 250 are connected to one another through an intrahospital network 260. The intrahospital network 160 (or 260) may be a special line connecting the electrocardiographs 110, 120 and 130 (or 210, 220 and 230), the electrocardiogram management system (EMS) 140 (or 240) and the display unit 150 (or 250) or may be a wire or wireless intranet line or a wire or wireless Internet line with security measures.

Each electrocardiograph 110, 120, 130, 210, 220, 230 has a function of retrieving personal coefficients of each patient or population coefficients, a function of calculating and storing the personal coefficients of the patient, and a function of generating a derived electrocardiogram of the patient. To this end, programs for fulfilling those functions are installed in the electrocardiograph 110, 120, 130, 210, 220, 230. Here, personal coefficients are conversion coefficients acquired from each specific patient. Population coefficients are average values of a plurality of conversion coefficients acquired from an unspecified large number of persons belonging to a statistically significant population. The personal coefficients or the population coefficients are used for generating a derived electrocardiogram of a patient.

The electrocardiogram management system 140 is mutually connected to the electrocardiographs 110, 120 and 130 through the intrahospital network 160. The electrocardiogram management system 140 exchanges information about derived electrocardiograms, such as patient information, generated electrocardiographic data, personal coefficients, etc., with the electrocardiographs 110, 120 and 130, and manages the information about the derived electrocardiograms. The electrocardiogram management system 240 is mutually connected to the electrocardiographs 210, 220 and 230 through the intrahospital network 260. The electrocardiogram management system 240 exchanges information about derived electrocardiograms, such as patient information, generated electrocardiographic data, personal coefficients, etc., with the electrocardiographs 210, 220 and 230, and manages the information about the derived electrocardiograms.

Each electrocardiogram management system 140, 240 has a function of retrieving personal coefficients of a patient requested through the connection network 400 by each electrocardiograph 110, 120, 130, 210, 220, 230, and outputting the retrieved personal coefficients to the requesting electrocardiograph. To this end, programs for fulfilling the function are installed in each electrocardiogram management system 140, 240.

The display unit 150 fetches, from the electrocardiogram management system 140, derived electrocardiograms of patients generated by the electrocardiographs 110, 120 and 130, and displays a derived electrocardiogram of a patient specified by an operator. In addition, the display unit 150 displays information about derived electrocardiograms obtained by the electrocardiographs 110, 120 and 130. The display unit 250 fetches, from the electrocardiogram management system 240, derived electrocardiograms of patients generated by the electrocardiographs 210, 220 and 230, and displays a derived electrocardiogram of a patient specified by an operator. In addition, the display unit 250 displays information about derived electrocardiograms obtained by the electrocardiographs 210, 220 and 230.

The patient ID management portion 300 has a function in which, when the electrocardiogram management systems 140 and 240 retrieve personal coefficients of one and the same specific patient, the patient ID management portion 300 converts an individual ID assigned to the patient by one hospital into an individual ID assigned to the other hospital. For example, assume that an individual ID "A123" is assigned to a patient in the hospital A, and an individual ID "B456" is assigned to the same patient in the hospital B. In this case, the individual ID "A123" is converted into the individual ID "B456", while the individual ID "B456" is converted into the individual ID "A123". A unique ID is used for converting one individual ID into another individual ID between the hospitals. The unique ID is only one ID assigned to the patient in the world. The ID is unique to the patient and can be shared and used among hospitals all over the world so that two unique IDs cannot be registered for one and the same patient. The patient ID management portion 300 has a comparison table where unique IDs can be compared with individual IDs. The comparison table is always updated in accordance with requests from the electrocardiogram management systems 140 and 240.

Figure 2:
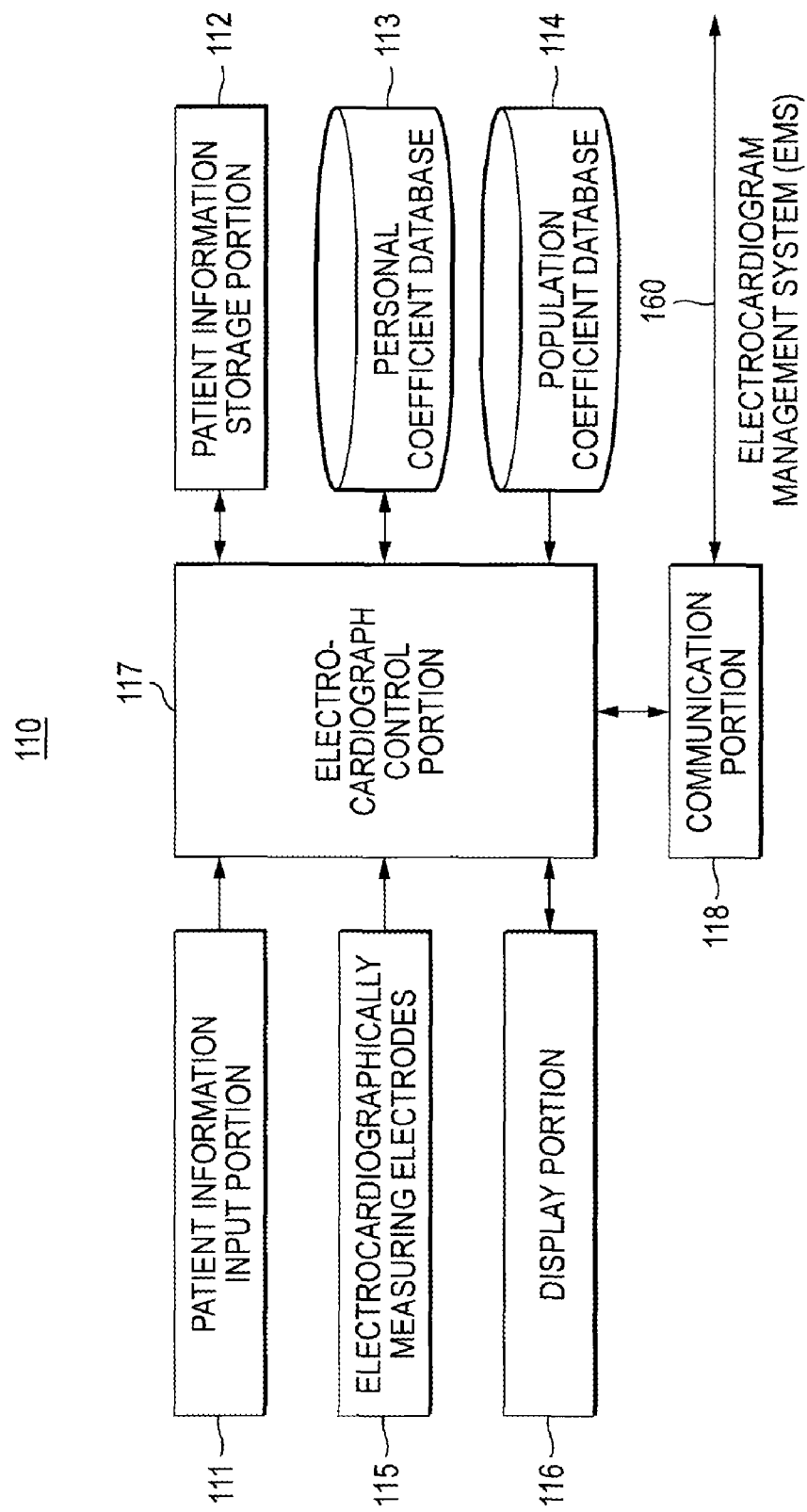
FIG. 2 is a block diagram of an electrocardiograph according to the embodiment.

FIG. 2 is a block diagram of an electrocardiograph according to the embodiment. The configuration of the electrocardiograph 110 will be described below. The configuration of each electrocardiograph 120, 130, 210, 220, 230 is the same as the configuration of the electrocardiograph 110.

The electrocardiograph 110 has a patient information input portion 111, a patient information storage portion 112, a personal coefficient database 113, a population coefficient database 114, electrocardiographically measuring electrodes 115, a display portion 116, an electrocardiograph control portion 117, and a communication portion 118.

The patient information input portion 111 inputs patient information. In accordance with keys operated by an operator, the patient information input portion 111 inputs a patient ID (unique ID and individual ID) (for acquiring personal coefficients), a patient name (for acquiring personal coefficients), a patient age (for acquiring population coefficients), a patient sex (for acquiring population coefficients), a measured lead number (for acquiring/storing personal coefficients), measured lead names (acquiring/storing personal coefficients), a derived lead number (for acquiring/storing personal coefficients), and derived lead names (for acquiring/storing personal coefficients). When the measured lead number, the measured lead names, the derived lead number and the derived lead names are inputted, a derived electrocardiogram type can be specified.

For example, in the hospital A, an operator inputs a unique ID "C123" and an individual ID "A123" as patient ID, and subsequently inputs a patient name, a patient age and a patient sex. When the operator wants to acquire a derived 12-lead electrocardiogram of the aforementioned type C, the operator inputs "12" as the measured lead number, "I, II, V2 and V5" as the measured lead names, "4" as the derived lead number, and "V1, V2, V4 and V6" as the derived lead names.

The patient information storage portion 112 stores patient information inputted by the patient information input portion 111. For example, in the aforementioned case, the unique ID "C123" of a patient, the individual ID "A123" of the patient, the patient name, the patient age, the patient sex, the measured lead number "12", the measured lead names "I, II, V2 and V5", the derived lead number "4" and the derived lead names "V1, V3, V4 and V6" are stored.

The personal coefficient database 113 stores personal coefficients specific to specified patients, which personal coefficients are acquired from the patients in advance and correspond to all the aforementioned eighteen derived electrocardiogram types (type A to type R) and custom-made derived electrocardiogram types other than the eighteen derived electrocardiogram types. The personal coefficients serve to generate derived electrocardiograms of portions effective in diagnosing heart diseases of the specified patients.

The personal coefficients of patients are stored in time series on a basis of each patient and each derived electrocardiogram type. For example, in the aforementioned case, the unique ID "C123" of the patient and the individual ID "A123" of the patient for specifying the patient and the measured lead number "12", the measured lead names "I, II, V2 and V5", the derived lead number "4" and the derived lead names "V1, V3, V4 and V6" for specifying the derived electrocardiogram type are added as additional information of the personal coefficients and stored in time series.

Normally, a latest data set of personal coefficients is sufficient to generate a derived electrocardiogram. Nevertheless a plurality of data sets of personal coefficients are stored in time series. This is because the progression of disease or the condition of recovery can be grasped by observation of a change between the data sets of personal coefficients or a change between derived electrocardiograms generated from the past personal coefficients and the current personal coefficients.

The population coefficient database 114 stores population coefficients which are average values of a plurality of conversion coefficients acquired from an unspecified large number of persons belonging to a statistically significant population in order to generate a standard derived electrocardiogram type (for example, a derived 12-lead electrocardiogram of the aforementioned type C) of each patient. As the population coefficients, the age of each patient, the sex of the patient and a derived electrocardiogram type are additionally stored as additional information of the population coefficients.

The electrocardiographically measuring electrodes 115 are electrodes to be attached to the body surface of a patient. The electrocardiographically measuring electrodes 115 are used for acquiring personal coefficients of the patient in order to acquire a derived electrocardiogram of the patient.

The display unit 116 displays, on a display, patient information inputted in the patient information input portion 111, or prints out a generated derived electrocardiogram.

The electrocardiograph control portion 117 generally controls the operation of the electrocardiograph 110. The electrocardiograph control portion 117 has a function of selecting personal coefficients of a patient from the personal coefficient database 113 or population coefficients from the population coefficient database 114, a function of calculating the personal coefficients of the patient and storing the personal coefficients into the personal coefficient database 113, and a function of generating a derived electrocardiogram of the patient using the selected personal or population coefficients. The electrocardiograph control portion 117 has programs for implementing those functions. The detailed operation of the electrocardiograph control portion 117 will be described later.

The communication portion 118 transmits personal coefficients of a patient to the electrocardiogram management system 140 and receives personal coefficients of a requested patient from the electrocardiogram management system 140. The personal coefficients are transmitted/received through the intrahospital network 160.

Figure 3:
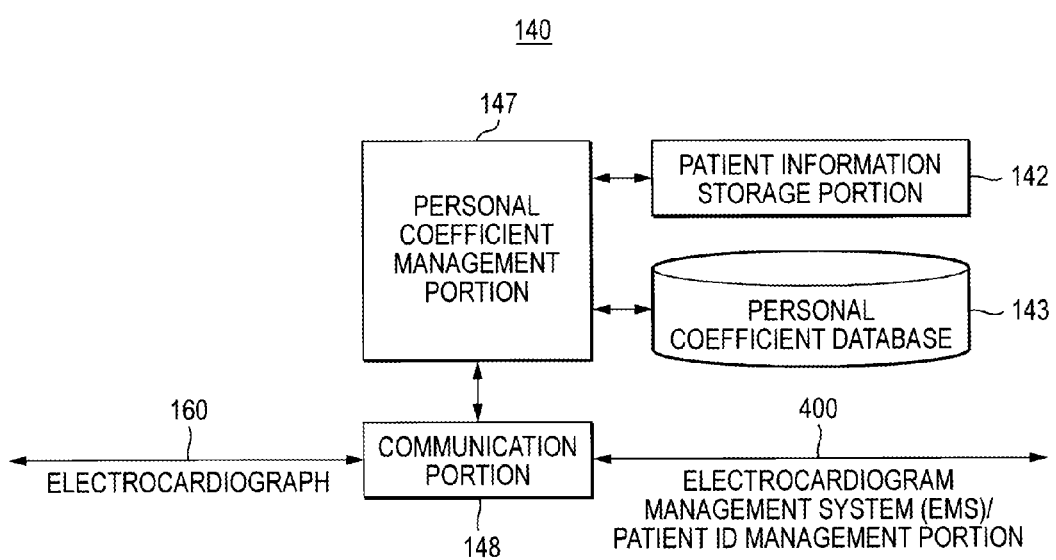
FIG. 3 is a block diagram of an electrocardiogram management system according to the embodiment.

FIG. 3 is a block diagram of the electrocardiogram management system according to the embodiment. The configuration of the electrocardiogram management system 140 will be described below. The configuration of the electrocardiogram management system 240 is the same as the configuration of the electrocardiogram management system 140.

The electrocardiogram management system 140 has a patient information storage portion 142, a personal coefficient database 143, a personal coefficient management portion 147 and a communication portion 148.

The patient information storage portion 142 stores the same patient information as the patient information stored by the patient information storage portions of the electrocardiographs 110, 120 and 130 (the patient information storage portion 112 in the electrocardiograph 110). The patient information storage portion 142 collectively stores all the patient information of the electrocardiographs 110, 120 and 130 connected to the intrahospital network 160.

The personal coefficient database 143 stores the same personal coefficients as the personal coefficients stored in the personal coefficient databases of the electrocardiographs 110, 120 and 130 (the personal coefficient database 113 in the electrocardiograph 110). The personal coefficient database 143 collectively stores all the personal coefficients of the electrocardiographs 110, 120 and 130 connected to the intrahospital network 160.

The personal coefficient management portion 147 generally controls the operation of the electrocardiograph management system 140. The personal coefficient management portion 147 has a function of storing patient information into the patient information storage portion 142 and a function of storing personal coefficients of a patient into the personal coefficient database 143 or retrieving personal coefficients of a patient from the personal coefficient database 143. The detailed operation of the personal coefficient management portion 147 will be described later.

The communication portion 148 receives patient information and personal coefficients from the electrocardiographs 110, 120 and 130 and transmits personal coefficients to the electrocardiographs 110, 120 and 130. Further, the communication portion 148 transmits a patient ID to the patient ID management portion 300 and receives a converted patient ID. The patient information and the personal coefficients are transmitted/received through the intrahospital network 160, and the patient ID is transmitted/received through the connection network 400.

Figure 4:
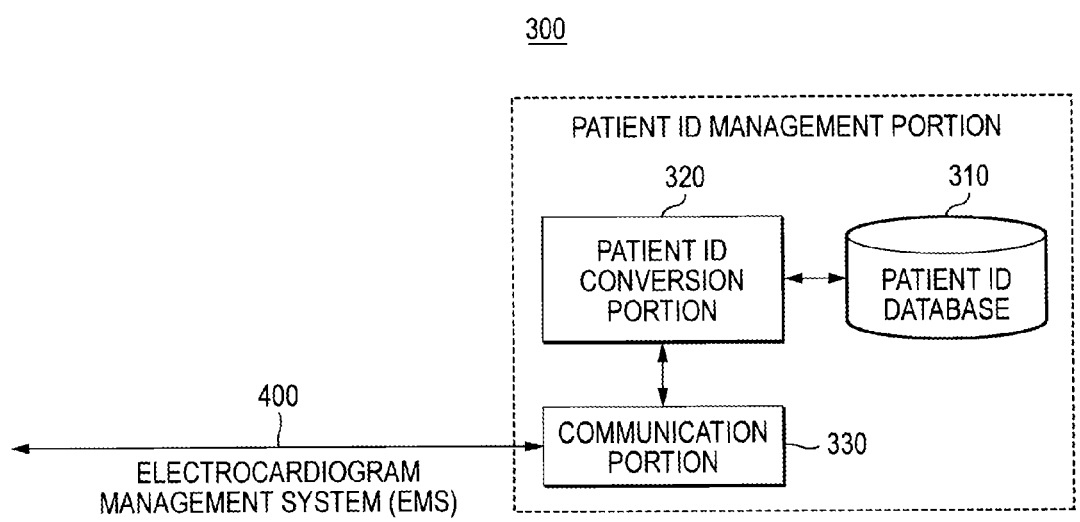
FIG. 4 is a block diagram of a patient ID management portion according to the embodiment.

FIG. 4 is a block diagram of the patient ID management portion according to the embodiment.

The patient ID management portion 300 has a patient ID database 310, a patient ID conversion portion 320 and a communication portion 330.

The patient ID database 310 stores a unique ID and an individual ID of each patient in association with each other. For example, assume that the unique ID is "C123", the individual ID in the hospital A is "A123" and the individual ID in the hospital B is "B456". In this case, those IDs are stored in the form of "C123"-"A123" and "C123"-"B456".

The patient ID conversion portion 320 converts an individual ID of a patient in one hospital to an individual ID of the patient in the other hospital with reference to a unique ID of the patient.

For example, assume that the hospital A seeks personal coefficients in the hospital B. In this case, the hospital A gains access to the patient ID database 310 with the help of the unique ID "C123", and converts the individual ID "A123" in the hospital A into the individual ID "B456" in the hospital B.

The communication portion 330 receives a unique ID and an individual ID of a patient from each electrocardiogram management system 140, 240, and transmits an individual ID converted by the patient ID conversion portion 320 to the electrocardiogram management system 140, 240.

The configuration of the derived electrocardiogram generating system according to the embodiment has been described above.

Figure 5:
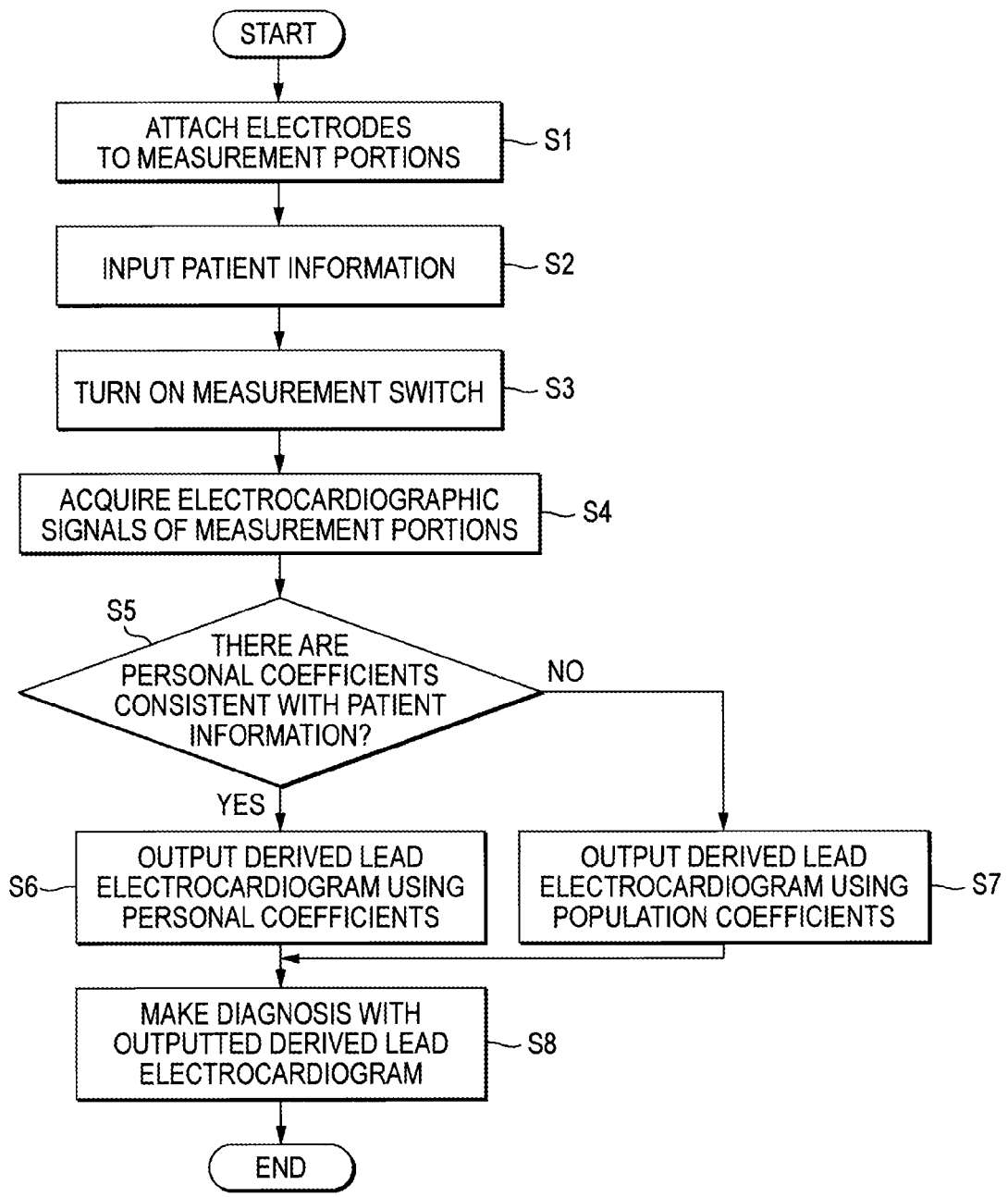
FIG. 5 is a flow chart showing the procedure of a derived electrocardiogram generating method according to the embodiment.

Next, the operation of the derived electrocardiogram generating system according to the embodiment will be described with reference to flow charts of FIGS. 5 and 6. In the flow chart of FIG. 5, an electrocardiograph operator carries out the operation of Steps S1 to S3 and Step S8, and the electrocardiograph control portion 117 carries out the operation of Steps S4 to S7. The operation of Steps S4 to S7 shows the procedure of the derived electrocardiogram generating method according to the embodiment. The operation of the electrocardiograph control portion 117 will be described on the assumption that a derived 12-lead electrocardiogram of the aforementioned type C is obtained.

First, the operator of the electrocardiograph 110 shown in FIG. 2 attaches the electrocardiographically measuring electrodes 115 to predetermined portions on the body surface of a patient. To obtain a derived 12-lead electrocardiogram of the aforementioned type C, the electrocardiographically measuring electrodes 115 are attached to a total of six measurement portions including four places of left and right arm portions (electrodes L and R) and left and right lower limbs (electrodes LL and RL) for acquiring electrocardiographic signals of leads I and II and two places where a fourth intercostal space at a left sternal border and a left anterior axillary line intersect with a horizontal line crossing a fifth intercostal space for acquiring electrocardiographic signals of two chest leads (leads V2 and V5) (Step S1).

Next, the operator inputs patient information through the patient information input portion 111. For example, in the hospital A, the operator inputs the unique ID "C123" and the individual ID "A123" as patient ID. Subsequently, the operator inputs a patient name, a patient age and a patient sex. Then, the operator inputs "12" as measured lead number, "I, II, V2 and V5" as measured lead names, "4" as derived lead number, and "V1, V3, V4 and V6" as derived lead names (Step S2).

Then, the operator turns on a measurement switch (not shown) of the electrocardiograph 110. As soon as the measurement switch is turned on, generating a derived electrocardiogram is started (Step S3).

The electrocardiograph control portion 117 acquires electrocardiographic signals of the measurement portions from the six electrocardiographically measuring electrodes 115 attached to the patient (Step S4).

Next, the electrocardiograph control portion 117 determines whether personal coefficients consistent with the patient information are present or not in the derived electrocardiogram generating system. Specifically, the electrocardiograph control portion 117 determines whether personal coefficients consistent with the unique ID "C123", the individual ID "A123", the measured lead number "12", the measured lead names "I, II, V2 and V5", the derived lead number "4" and the derived lead names "V1, V3, V4 and V6" inputted through the patient information input portion 111 are present or not in the personal coefficient database 113 or 143 or the personal coefficient database of the electrocardiogram management system 240. As for the retrieval order, the electrocardiograph control portion 117 retrieves the personal coefficients first from the personal coefficient database 113 of the electrocardiograph 110, next from the personal coefficient database 143 of the electrocardiogram management system 140 in the hospital A, and finally from the personal coefficient database of the electrocardiogram management system 240 in the hospital B. Although the personal coefficients are retrieved in that order in this embodiment, the order may be replaced by any desired order.

To retrieve the personal coefficients from the personal coefficient database of the electrocardiogram management system 240, the individual ID "A123" in the hospital A is converted into the individual ID "B456" in the hospital B by the patient ID management portion 300 because the personal coefficient database is disposed in the electrocardiogram management system 240 of the hospital B. The conversion of the individual ID "A123" to the individual ID "B456" is carried out based on the unique ID "C123". Then, the electrocardiograph control portion 117 determines whether personal coefficients consistent with the converted individual ID "B456", the measured lead number "12", the measured lead names "I, II, V2 and V5", the derived lead number "4" and the derived lead names "V1, V3, V4 and V6" are present or not in the personal coefficient database of the electrocardiogram management system 240 (Step S5).

When personal coefficients consistent with the patient information are present in any one of the personal coefficient databases 113 and 143 and the personal coefficient database of the electrocardiogram management system 240, the electrocardiograph control portion 117 acquires the personal coefficients from any one of the personal coefficient databases 113 and 143 and the personal coefficient database of the electrocardiogram management system 240. When there are a plurality of data sets of personal coefficients (YES in Step S5), the electrocardiograph control portion 117 acquires the latest data set of personal coefficients. The electrocardiograph control portion 117 uses the acquired personal coefficients to generate and output a derived 12-lead electrocardiogram of the type C based on electrocardiographic signals obtained from the six electrocardiographically measuring electrodes 115. The derived electrocardiogram generated on this occasion is a derived 12-lead electrocardiogram which is the most suitable to the patient because the coefficients specific to the patient are used (Step S6).

When personal coefficients consistent with the patient information are not present in any one of the personal coefficient databases 113 and 143 and the personal coefficient database of the electrocardiogram management system 240 (NO in Step 5), the electrocardiograph control portion 117 acquires, from the population coefficient database 114, population coefficients consistent with the patient age, the patient sex, the measured lead number "12", the measured lead names "I, II, V2 and V5", the derived lead number "4" and the derived lead names "V1, V3, V4 and V6" inputted as the patient information. Then, the electrocardiograph control portion 117 uses the acquired population coefficients to generate and output a derived 12-lead electrocardiogram of the type C based on electrocardiographic signals obtained from the six electrocardiographically measuring electrodes 115. The derived electrocardiogram generated on this occasion is a derived 12-lead electrocardiogram having average accuracy (Step S7).

Finally, the operator, a diagnostician or an automatic diagnosis program diagnoses the existence or degree of heart disease of the patient in view of electrocardiographic waveforms in the derived 12-lead electrocardiogram of the type C outputted by the electrocardiograph 110 (Step S8).

As described above, the electrocardiograph 110 generates a derived electrocardiogram using personal coefficients of a patient when the personal coefficients are present, and generates a derived electrocardiogram using population coefficients of the patient when the personal coefficients are not present.

Accordingly, when personal coefficients of a patient having a unique heart are stored in the personal coefficient database 113 or 143 in advance, a derived electrocardiogram of portions effective in diagnosing heart disease of the patient can be generated with high accuracy. In addition, even when the personal coefficients of the patient are absent, a standard derived electrocardiogram can be obtained using population coefficients. In this case, a derived electrocardiogram having average accuracy can be obtained. In any case, a derived electrocardiogram which is clinically practical can be obtained without failure.

In order that a derived electrocardiogram of portions effective in diagnosing heart disease of a patient can be obtained, personal coefficients specific to the patient have to be created and stored in the personal coefficient database 113 or 143 in advance. Next, the procedure up to the steps in which personal coefficients are calculated by the electrocardiograph control portion 117 and stored in the personal coefficient databases 113 and 143 will be described with reference to the flow chart of FIG. 6.

Figure 6:
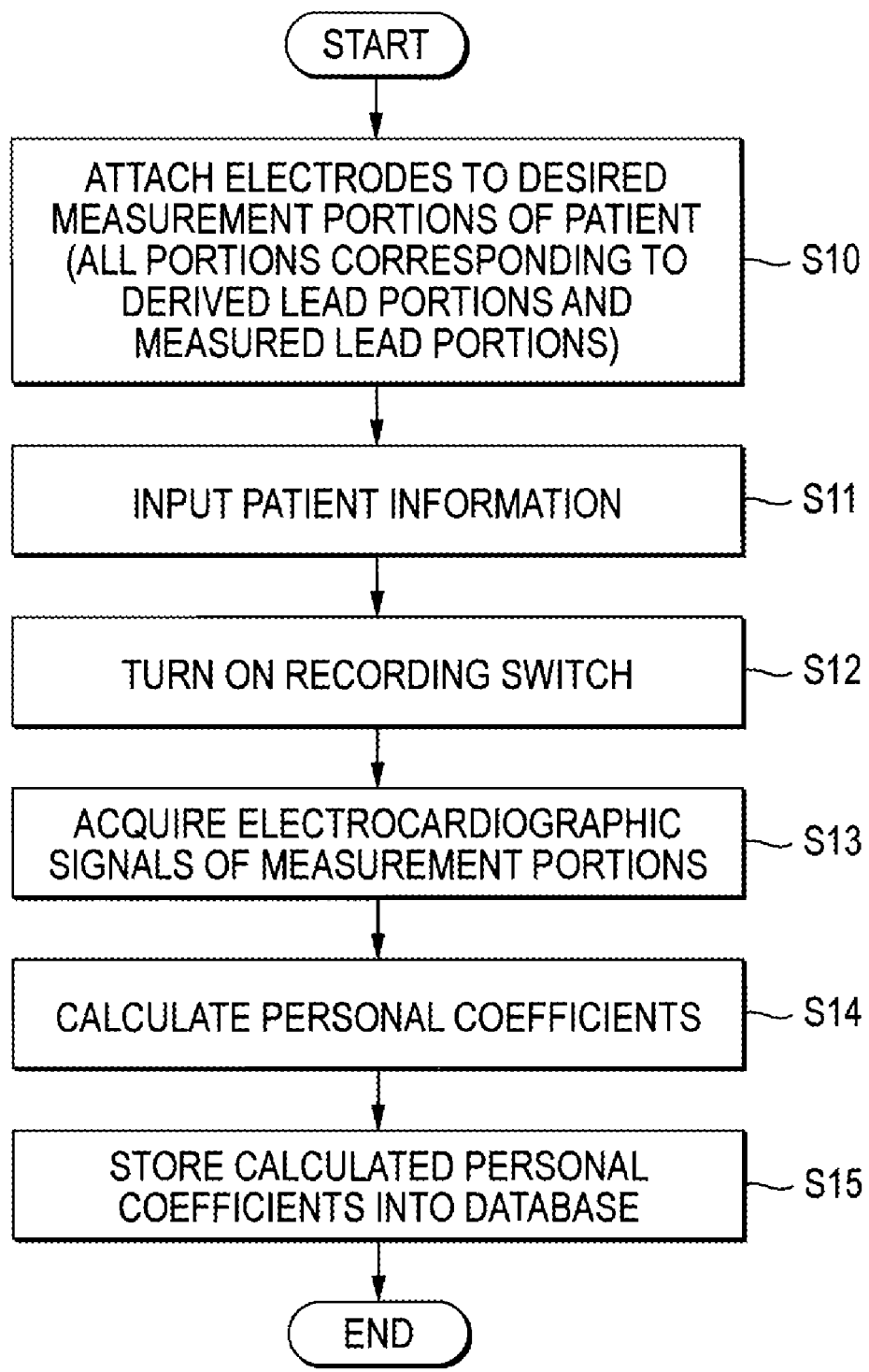
FIG. 6 is a flowchart showing the procedure of the derived electrocardiogram generating method according to the embodiment.

In the flow chart of FIG. 6, the operator of the electrocardiograph carries out the operation of Steps S10 to S12, and the electrocardiograph control portion 117 carries out the operation of Steps S13 to S15. The operation of Steps S13 to S15 shows the procedure of the derived electrocardiogram generating method according to the embodiment. The operation of the electrocardiograph control portion 117 will be described on the assumption that a derived 12-lead electrocardiogram of the aforementioned type C is obtained.

First, the operator of the electrocardiograph 110 shown in FIG. 2 attaches the electrocardiographically measuring electrodes 115 to desired portions on the body surface of the patient. To obtain personal coefficients for a derived 12-lead electrocardiogram of the aforementioned type C, the electrocardiographically measuring electrodes 115 are attached to ten places on the body surface of the patient corresponding to derived lead portions and measured lead portions. The places where the electrocardiographically measuring electrodes 115 are attached are portions where the electrocardiographically measuring electrodes 115 can acquire ten electrocardiographic signals of leads I, II, V1, V2, V3, V4, V5 and V6. To obtain personal coefficients of another derived electrocardiogram type, the electrocardiographically measuring electrodes 115 are attached to desired portions where a derived electrocardiogram effective in diagnosing the patient can be generated (Step S10).

Next, the operator inputs patient information through the patient information input portion 111. For example, in the hospital A, the operator inputs a unique ID "C123" and an individual ID "A123" as patient ID, and subsequently inputs a patient name, a patient age and a patient sex. Then, the operator inputs "12" as the measured lead number, "I, II, V2 and V5" as the measured lead names, "4" as the derived lead number, and "V1, V3, V4 and V6" as the derived lead names (Step S11).

Then, the operator turns on the measurement switch (not shown) of the electrocardiograph 110 (Step S12). The electrocardiograph control portion 117 acquires electrocardiographic signals of the measurement portions from the ten electrocardiographically measuring electrodes 115 attached to the patient. Leads V1, V3, V4 and V6 as derived lead vectors and leads I, II, V2 and V5 as measured lead vectors can be actually measured from the ten electrocardiographically measuring electrodes 115 (Step S13).

The electrocardiograph control portion 117 substitutes the leads actually measured by the ten electrocardiographically measuring electrodes 115 into the aforementioned determinant to calculate personal coefficients of the patient (Step S14). The electrocardiograph control portion 117 stores the calculated personal coefficients into the personal coefficient database 113, and at the same time stores the personal coefficients into the personal coefficients database 143 of the electrocardiogram management system 140. When the personal coefficients are stored, the unique ID "C123" of the patient, the individual ID "A123" of the patient, the measured lead number "12", the measured lead names "I, II, V2 and V5", the derived lead number "4" and the derived lead names "V1, V3, V4 and V6" are added as additional information of the personal coefficients and stored in time series (Step S15).

The schematic operation of the derived electrocardiogram generating system and the derived electrocardiogram generating method according to the embodiment has been described above.

Next, the operation of the derived electrocardiogram generating system according to the embodiment will be described further in detail with reference to flow charts of FIGS. 7 to 14.

Figure 7:
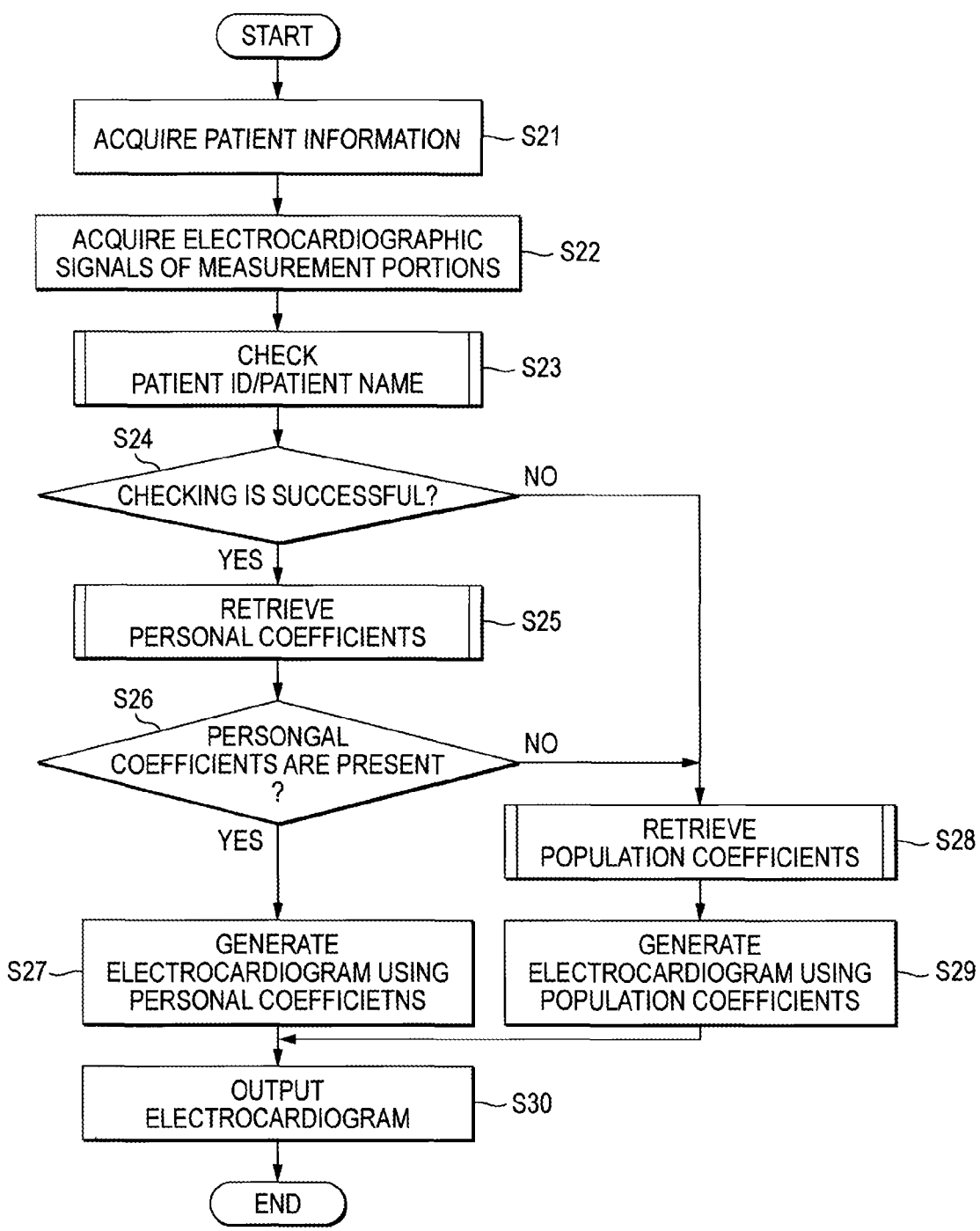
FIG. 7 is a main flow chart showing processing up to the step in which the electrocardiograph outputs a derived electrocardiogram of a patient.

FIG. 7 is a main flow chart showing processing up to the step in which the electrocardiograph 110 outputs a derived electrocardiogram of a patient. The main flow chart is processed by the electrocardiograph control portion 117 of the electrocardiograph 110.

The electrocardiograph control portion 117 acquires patient information inputted through the patient information input portion 111. The patient information includes a patient ID (unique ID and individual ID), a patient name, a patient age, a patient sex, a measured lead number, measured lead names, a derived lead number, and derived lead names. The measured lead number, the measured lead names, the derived lead number and the derived lead names show a derived electrocardiogram type. The patient ID, the measured lead number, the measured lead names, the derived lead number and the derived lead names are used for retrieving personal coefficients of the patient. The patient age, the patient sex, the measured lead number, the measured lead names, the derived lead number and the derived lead names are used for retrieving population coefficients (Step S21).

The electrocardiograph control portion 117 acquires electrocardiographic signals of measurement portions from a plurality of electrocardiographically measuring electrodes 115 attached to the patient (Step S22). The electrocardiograph control portion 117 checks the patient ID and the patient name with patient IDs and patient names stored in the patient information storage portion 112 (Step S23).

When a consistent patient ID and a consistent patient name are present in the patient information storage portion 112, checking is successful (YES in Step S24). In this case, personal coefficients stored in the personal coefficient database 113 or 143 or the personal coefficient database of the electrocardiogram management system 240 are retrieved (Step S25).

When personal coefficients of the patient are present in any one of the personal coefficient databases 113 and 143 and the personal coefficient database of the electrocardiogram management system 240 (YES in Step S26), the electrocardiograph control portion 117 acquires the personal coefficients of the patient from any one of the personal coefficient databases 113 and 143 and the personal coefficient database of the electrocardiogram management system 240. The electrocardiograph control portion 117 uses the acquired personal coefficients to process the electrocardiographic signals acquired by the electrocardiographically measuring electrodes 115 so as to generate a derived electrocardiogram (Step S27).

On the other hand, when a consistent patient ID and a consistent patient name are not present in the patient information storage portion 112 (NO in Step S24) or when personal coefficients of the patient are not present in any one of the personal coefficient databases 113 and 143 and the personal coefficient database of the electrocardiogram management system 240 (NO in Step 26), the electrocardiograph control portion 117 retrieves population coefficients stored in the population coefficient database 114 (Step S28).

In view of the sex and age of the patient and the derived electrocardiogram type, the electrocardiograph control portion 117 acquires, from the population coefficient database 114, population coefficients which are the most suitable to the patient. The electrocardiograph control portion 117 uses the acquired population coefficients to process the electrocardiographic signals acquired by the electrocardiographically measuring electrodes 115 so as to generate a derived electrocardiogram (Step S29). The electrocardiograph control portion 117 outputs the generated derived electrocardiogram to the display portion 116 (Step S30).

Figure 8:
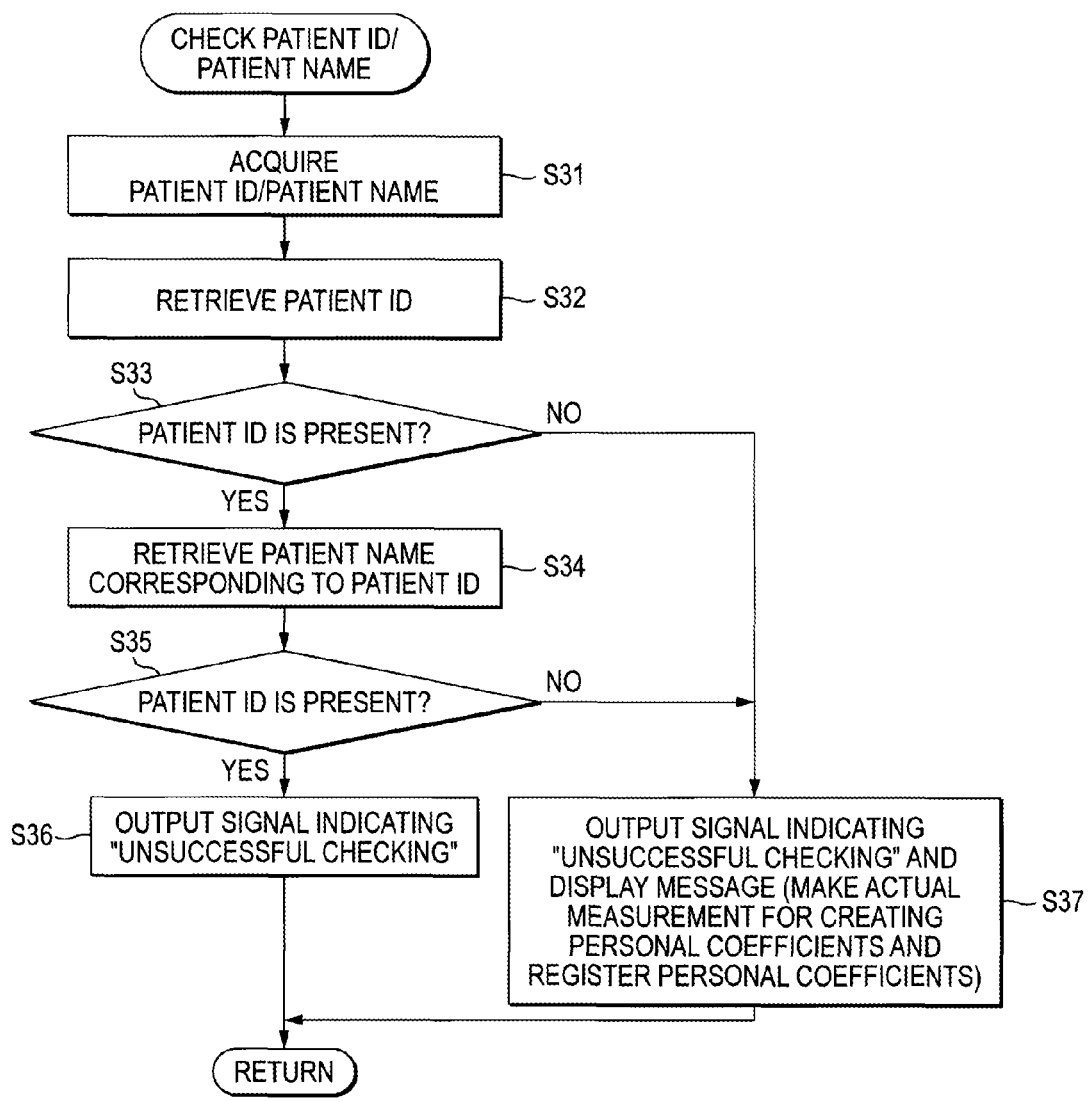
FIG. 8 is a subroutine flow chart of Step S23 (checking patient ID/patient name) in the main flow chart of FIG. 7.

FIG. 8 is a subroutine flow chart of Step S23 (checking patient ID/patient name) in the main flow chart of FIG. 7. The subroutine flow chart is processed by the electrocardiograph control portion 117.

The electrocardiograph control portion 117 acquires the patient ID and the patient name from the patient information inputted through the patient information input portion 111 (Step S31). The electrocardiograph control portion 117 retrieves patient IDs stored in the patient information storage portions 112 and 142 (Step S32). When the same patient ID as the patient ID inputted through the patient information input portion 111 is present in any one of the patient information storage portions 112 and 142 (YES in Step S33), the electrocardiograph control portion 117 retrieves patient names stored in the patient information storage portion 112 (Step S34). When the same patient name as the patient name inputted through the patient information input portion 111 is present in anyone of the patient information storage portions 112 and 142 (YES in Step S35), the electrocardiograph control portion 117 outputs a signal indicating successful checking (Step S36). When the same patient ID as the patient ID inputted through the patient information input portion 111 is not present in any one of the patient information storage portions 112 and 142 (NO in Step S33) or when the same patient name as the patient name inputted through the patient information input portion 111 is not present in any one of the patient information storage portions 112 and 142 (NO in Step S35), the electrocardiograph control portion 117 outputs a signal indicating unsuccessful checking and displays a message "Make actual measurement for creating personal coefficients and register the personal coefficients" on the display portion 116 (Step S37).

That is, checking is regarded as successful when the inputted patient ID and the inputted patient name is consistent with a patient ID and a patient name registered in the electrocardiograph 110 or the electrocardiogram management system 140, and checking is regarded as unsuccessful when either the inputted patient ID or the inputted patient name is consistent with a patient ID and a patient name registered in the electrocardiograph 110 or the electrocardiogram management system 140. When checking is unsuccessful, personal coefficients of the patient have not been stored in the personal coefficient databases 113 and 143. Thus, a message to prompt acquisition of personal coefficients is outputted.

Figure 9:
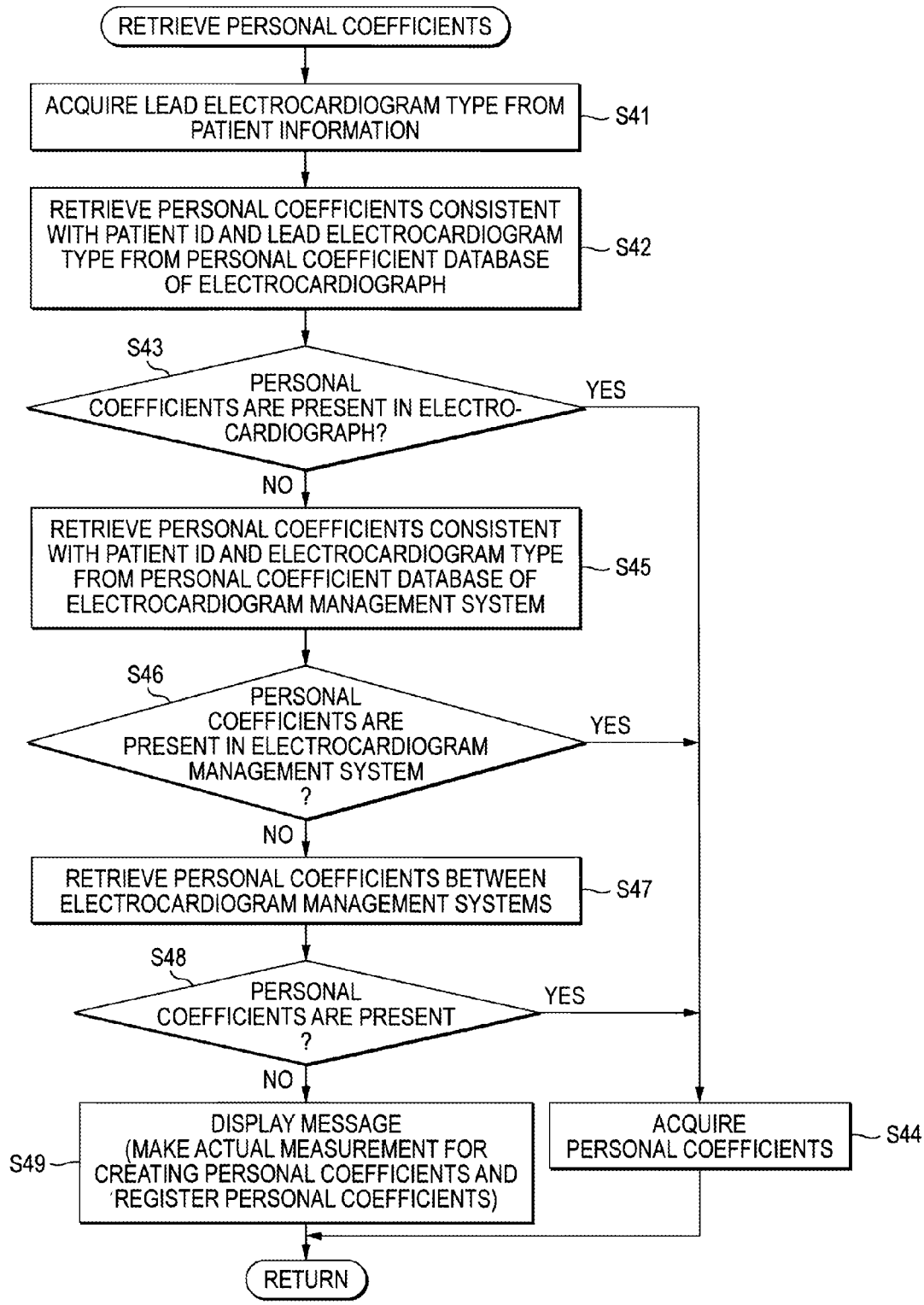
FIG. 9 is a subroutine flowchart of Step S25 (retrieving personal coefficients) in the main flow chart of FIG. 7.

FIG. 9 is a subroutine flowchart of Step S25 (retrieving personal coefficients) in the main flow chart of FIG. 7. The subroutine flow chart is processed by the electrocardiograph control portion 117.

The electrocardiograph control portion 117 acquires the derived electrocardiogram type from the patient information inputted through the patient information input portion 111. For example, when a derived electrocardiogram of the type C is specified, the electrocardiograph control portion 117 acquires the measured lead number "12", the measured lead names "I, II, V2 and V5", the derived lead number "4" and the derived lead names "V1, V3, V4 and V6" (Step S41). Next, the electrocardiograph control portion 117 retrieves personal coefficients consistent with the patient ID and the derived electrocardiogram type from the personal coefficient database 113 of the electrocardiograph 110. That is, the electrocardiograph control portion 117 performs retrieval to find out whether personal coefficients consistent with the derived electrocardiogram type specified by the patient are present or not in the electrocardiograph 110 (Step S42). When personal coefficients consistent with the derived electrocardiogram type specified by the patient are present in the electrocardiograph 110 (YES in Step S43), the electrocardiograph control portion 117 acquires the personal coefficients from the personal coefficient database 113 (Step S44).

On the other hand, when personal coefficients consistent with the derived electrocardiogram type specified by the patient are not present in the personal coefficient database 113 of the electrocardiograph 110 (NO in Step S43), the electrocardiograph control portion 117 retrieves personal coefficients consistent with the patient ID and the derived electrocardiogram type from the personal coefficient database 143 of the electrocardiogram management system 140. That is, the electrocardiograph control portion 117 performs retrieval to find out whether personal coefficients consistent with the type specified by the patient are present or not in the electrocardiogram management system 140 (Step S45). When personal coefficients consistent with the type specified by the patient are present in the electrocardiogram management system 140 (YES in Step S46), the electrocardiograph control portion 117 acquires the personal coefficients from the personal coefficient database 143 (Step S44).

On the other hand, when personal coefficients consistent with the derived electrocardiogram type specified by the patient are not present in the personal coefficient database 143 of the electrocardiogram management system 140 (NO in Step S46), the electrocardiograph control portion 117 retrieves personal coefficients consistent with the patient ID and the derived electrocardiogram type between the electrocardiogram management systems 140 and 240. In this embodiment, the electrocardiograph control portion 117 retrieves personal coefficients consistent with the patient ID and the derived electrocardiogram type from the electrocardiogram management system 240. Retrieval of personal coefficients between the electrocardiogram management systems 140 and 240 is carried out using an individual ID converted with the unique ID of the patient by the patient ID conversion portion 320 (Step S47). When personal coefficients consistent with the derived electrocardiogram type specified by the patient are present in the personal coefficient database of the electrocardiogram management system 240 (YES in Step S43), the electrocardiograph control portion 117 acquires the personal coefficients from the personal coefficient database of the electrocardiogram management system 240 (Step S44).

When the personal coefficients are not present in the personal coefficient database of the electrocardiogram management system 240, the electrocardiograph control portion 117 displays a message "Make actual measurement for creating personal coefficients and register the personal coefficients" on the display portion 116 (Step S49).

Figure 10:
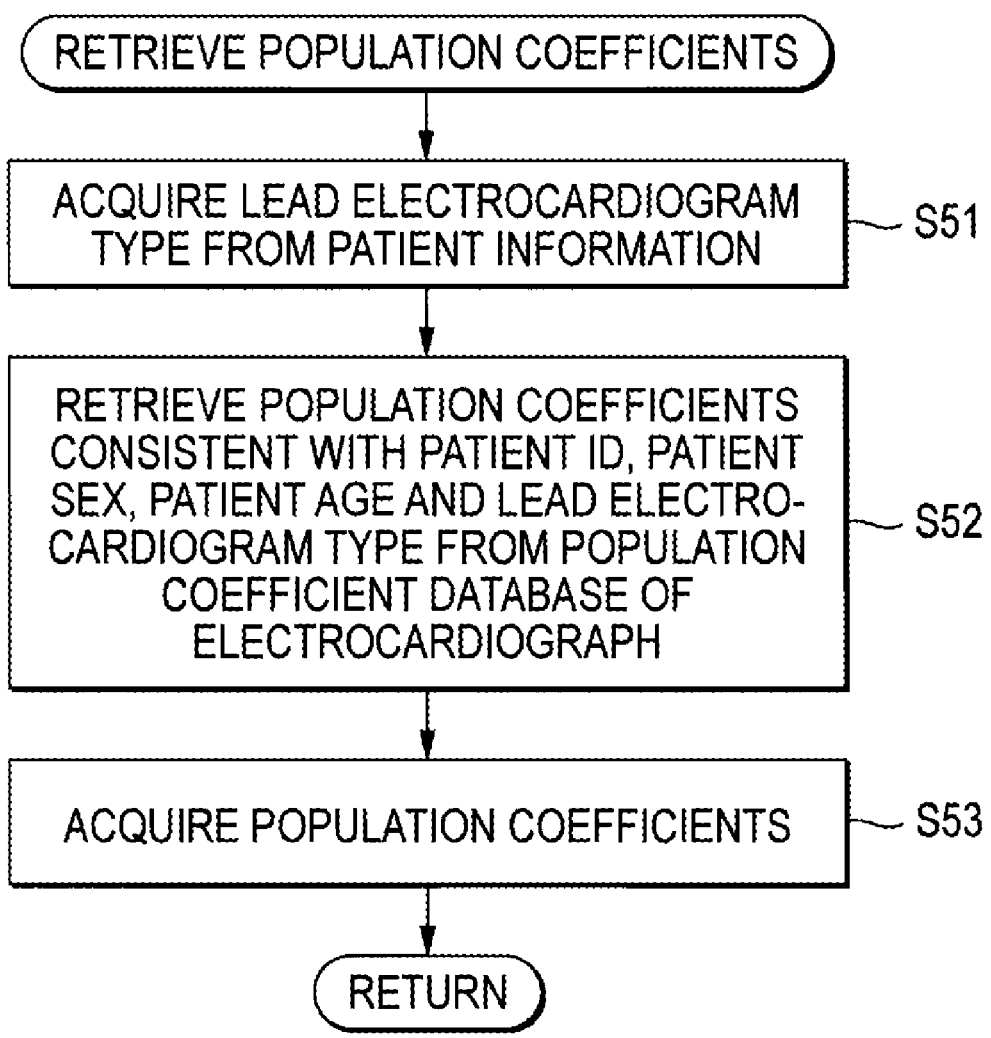
FIG. 10 is a subroutine flowchart of Step S28 (retrieving population coefficients) in the main flow chart of FIG. 7.

FIG. 10 is a subroutine flow chart of Step S28 (retrieving population coefficients) in the main flow chart of FIG. 7. The subroutine flow chart is processed by the electrocardiograph control portion 117.

The electrocardiograph control portion 117 acquires the derived electrocardiogram type from the patient information inputted through the patient information input portion 111. For example, when a derived electrocardiogram of the type C is specified, the electrocardiograph control portion 117 acquires the measured lead number "12", the measured lead names "I, II, 72 and 75", the derived lead number "4" and the derived lead names "V1, V3, V4 and V6" (Step S51).

Next, the electrocardiograph control portion 117 retrieves population coefficients consistent with the patient ID, the patient sex, the patient age and the derived electrocardiogram type from the population coefficient database 114 of the electrocardiograph 110. That is, the electrocardiograph control portion 117 performs retrieval to find out whether population coefficients consistent with the derived electrocardiogram type specified by the patient are present or not in the electrocardiograph 110 (Step S52). The electrocardiograph control portion 117 acquires the population coefficients from the population coefficient database 114 of the electrocardiograph 110 (Step S53).

Figure 11:
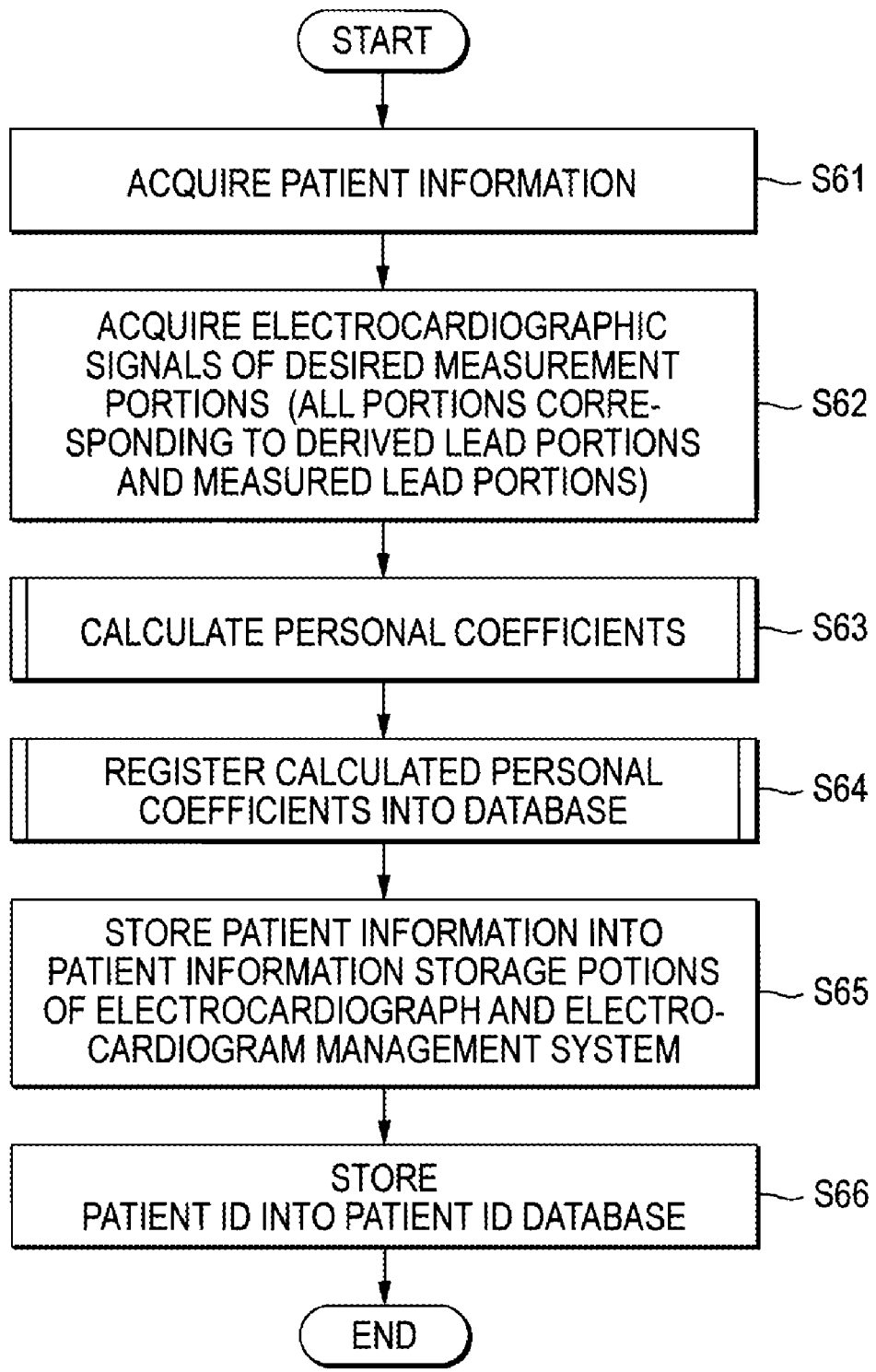
FIG. 11 is a main flow chart showing processing up to the step in which personal coefficients of a patient are calculated and the calculated personal coefficients are stored in a personal coefficient database.

FIG. 11 is a main flowchart showing processing up to the steps in which personal coefficients of a patient are calculated and the calculated personal coefficients are stored into a personal coefficient database. The main flow chart is processed by the electrocardiograph control portion 117.

The electrocardiograph control portion 117 acquires patient information inputted through the patient information input portion 111. The patient information includes a patient ID (unique ID and individual ID), a patient name, a patient age, a patient sex, a measured lead number, measured lead names, a derived lead number, and derived lead names. The measured lead number, the measured lead names, the derived lead number and the derived lead names show a derived electrocardiogram type. The patient ID, the measured lead number, the measured lead names, the derived lead number and the derived lead names are used for storing personal coefficients of the patient into each personal coefficient database (Step S61).

The electrocardiograph control portion 117 acquires electrocardiographic signals of desired measurement portions from a plurality of electrocardiographically measuring electrodes 115 attached to the patient. To calculate personal coefficients of a derived 12-lead electrocardiogram of the type C, the electrocardiographically measuring electrodes 115 are attached to ten places on the body surface of the patient corresponding to derived lead portions and measured lead portions. The places where the electrocardiographically measuring electrodes 115 are attached are portions where the electrocardiographically measuring electrodes 115 detect ten electrocardiographic signals of leads I, II, V1, V2, V3, V4, V5 and V6. The electrocardiograph control portion 117 actually measures leads V1, V3, V4 and V6 as derived lead vectors and leads I, II, V2 and V5 as measured lead vectors from the ten electrocardiographically measuring electrodes 115 (Step S62).

The electrocardiograph control portion 117 substitutes the leads actually measured by the ten electrocardiographically measuring electrodes 115 into the aforementioned determinant to calculate personal coefficients of the patient (Step S63).

Next, the electrocardiograph control portion 117 stores the calculated personal coefficients into the database of the derived electrocardiogram generating system in time series on a basis of each derived electrocardiogram type and each patient (Step S64).

The electrocardiograph control portion 117 stores the patient information acquired in Step S61 into the patient information storage portion 112 of the electrocardiograph 110 and at the same time stores the patient information into the patient information storage portion 142 of the electrocardiogram management system 140. To store the patient information into the patient information storage portion 142, the electrocardiograph control portion 117 transmits the patient information through the communication portion 118 by the intrahospital network 160 so that the personal coefficient management portion 147 receives the patient information through the communication portion 148 of the electrocardiogram management system 140. Then, the patient information received by the personal coefficient management portion 147 is stored into the patient information storage portion 142 (Step S65). Then, the electrocardiograph control portion 117 stores the patient ID (unique ID and individual ID) of the patient information acquired in Step S61 into the patient ID database 310 of the patient ID management portion 300. To store the patient ID into the patient ID database 310, the electrocardiograph control portion 117 transmits the patient ID through the communication portion 118 by the intrahospital network 160 and the connection network 400 so that the patient ID conversion portion 320 receives the patient ID through the communication portion 330 of the patient ID management portion 300. Then, the patient ID received by the patient ID conversion portion 320 is stored into the patient ID database 310 (Step S66).

Figure 12:
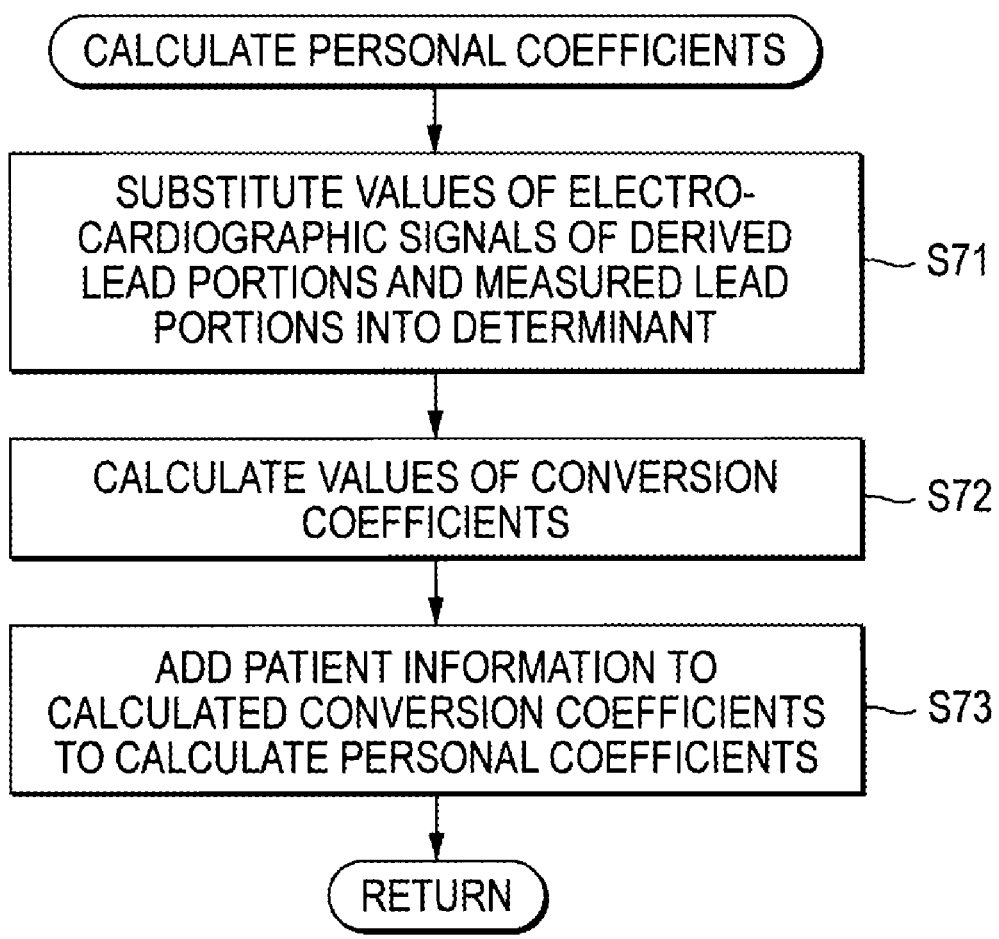
FIG. 12 is a subroutine flow chart showing processing of Step S63 (calculating personal coefficients) in the main flow chart of FIG. 11.

FIG. 12 is a subroutine flow chart showing processing of Step S63 (calculating personal coefficients) in the main flow chart of FIG. 11. The subroutine flow chart is processed by the electrocardiograph control portion 117.

The electrocardiograph control portion 117 substitutes the leads actually measured by the ten electrocardiographically measuring electrodes 115, that is, the leads V1, V3, V4 and V6 as derived lead vectors and the leads I, II, V2 and V5 as measured lead vectors, into the aforementioned determinant (Step S71). Then, the electrocardiograph control portion 117 calculates values of conversion coefficients from the values of the leads V1, V3, V4 and V6 and the values of the leads I, II, V2 and V5 (Step S72). Finally, the electrocardiograph control portion 117 adds patient information to the calculated conversion coefficients to calculate personal coefficients. Specifically, the added patient information includes a measured lead number, measured lead names, a derived lead number and derived lead names showing a derived electrocardiogram type, as well as a patient ID (unique ID and individual ID). In the aforementioned case, the unique ID "C123" of the patient, the individual ID "A123" of the patient, the measured lead number "12", the measured lead names "I, II, V2 and V5", the derived lead number "4" and the derived lead names "V1, V3, V4 and V6" are added as additional information to calculate personal coefficients (Step S73).

Figure 13:
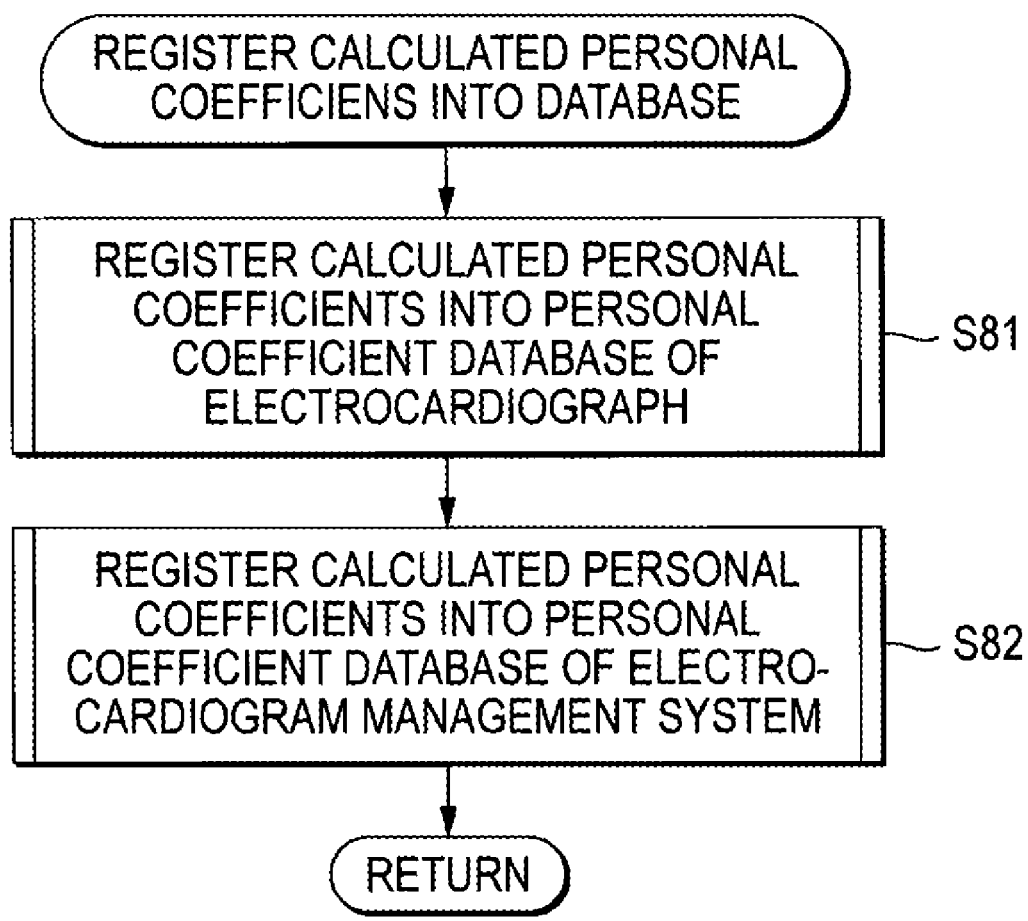
FIG. 13 is a subroutine flow chart showing processing of Step S64 (registering the calculated personal coefficients in the database) in the main flow chart of FIG. 11.

FIG. 13 is a subroutine flow chart showing processing of Step S64 (registering the calculated personal coefficients into the database) in the main flow chart of FIG. 11. The subroutine flow chart is processed by the electrocardiograph control portion 117 and the personal coefficient management portion 147.

First, the electrocardiograph control portion 117 stores the calculated personal coefficients into the personal coefficient database 113 (Step S81). Then, the personal coefficient management portion 147 stores the personal coefficients transmitted from the electrocardiograph control portion 117 into the personal coefficient database 143 (Step S82). The detailed processing of those steps is shown in subroutine flow charts of FIGS. 14 and 15.

Figure 14:
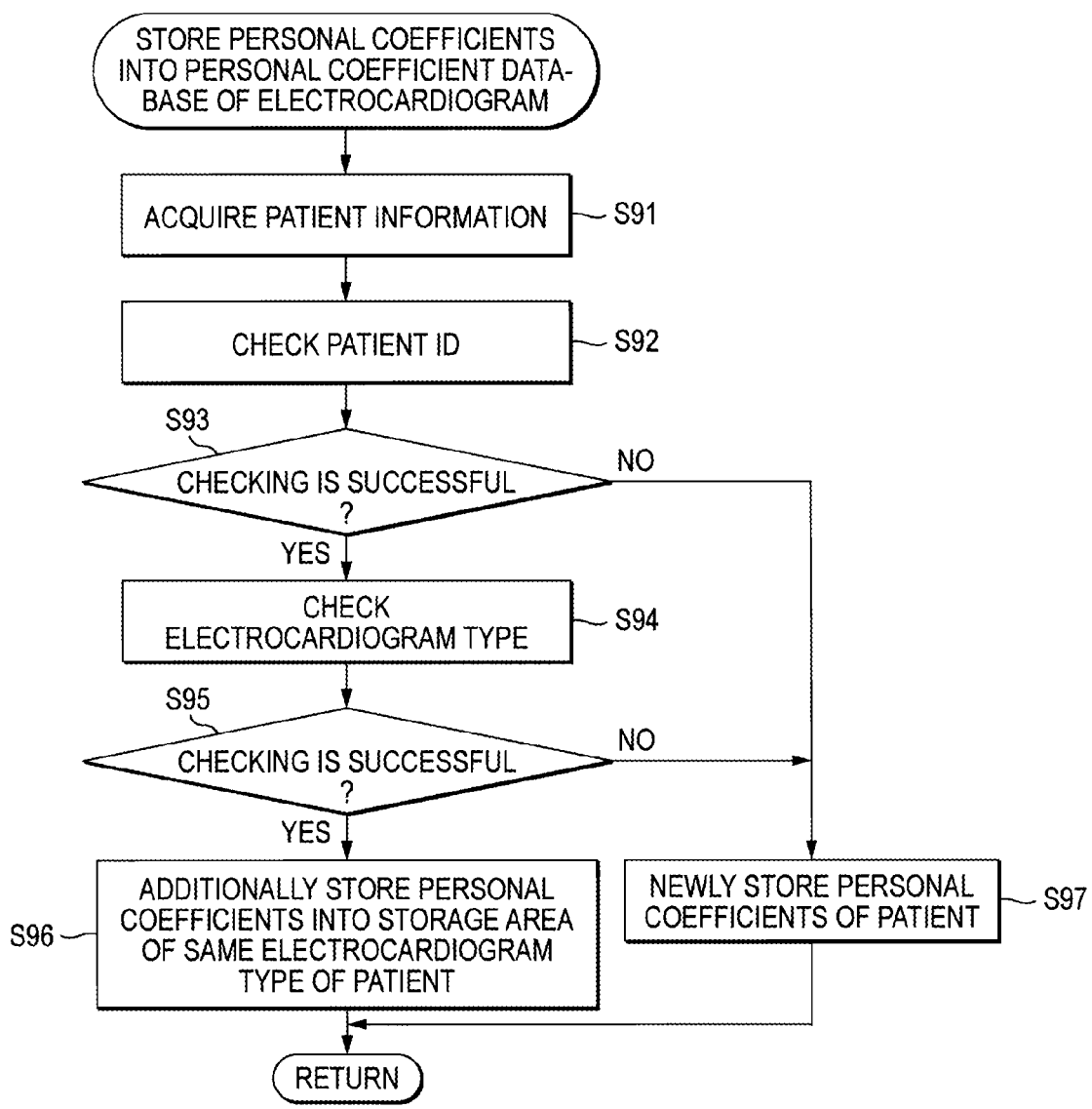
FIG. 14 is a subroutine flow chart showing processing of Step S81 (storing the personal coefficients into the personal coefficient database of the electrocardiograph) in the subroutine flow chart of FIG. 13.

FIG. 14 is a subroutine flow chart showing processing of Step S81 (storing the personal coefficients into the personal coefficient database of the electrocardiograph) in the subroutine flow chart of FIG. 13. The subroutine flow chart is processed by the electrocardiograph control portion 117.

First, the electrocardiograph control portion 117 acquires patient information inputted through the patient information input portion 111. The patient information includes a patient ID (unique ID and individual ID), a patient name, a patient age, a patient sex, a measured lead number, measured lead names, a derived lead number, and derived lead names (Step S91). The electrocardiograph control portion 117 checks the patient ID with patient IDs stored in the patient information storage portion 112 (Step S92). When a consistent patient ID is present in the patient information storage portion 112, checking is successful (YES in Step S93). In this case, the electrocardiograph control portion 117 checks derived electrocardiogram types of personal coefficients stored in the patient information storage portion 112. The derived electrocardiogram types are checked using the measured lead number, the measured lead names, the derived lead number, and the derived lead names (Step S94). When personal coefficients of a consistent derived electrocardiogram type are present in the personal coefficient database 113, checking is successful (YES in Step S95) in this case, the electrocardiograph control portion 117 additionally stores the personal coefficients into a storage area of the same derived electrocardiogram type of the patient in the personal coefficient database 113. That is, when the same patient has already had personal coefficients of the same derived electrocardiogram type, the electrocardiograph control portion 117 stores the newly calculated personal coefficients additionally in time series (Step S96). When the personal coefficients are updated in time series, coefficients the most suitable to the heart condition of the patient can be always selected to generate a high-accuracy derived electrocardiogram.

On the other hand, when a consistent patient ID is not present in the patient information storage portion 112 so that checking is unsuccessful (NO in Step S93) or when personal coefficients of a consistent electrocardiogram type are not present in the personal coefficient database 113 so that checking is unsuccessful (NO in Step S95), the electrocardiograph control portion 117 stores the personal coefficients into the personal coefficient database 113 newly (Step S97) because the personal coefficients of the patient are absent in the personal coefficient database 113.

Figure 15:
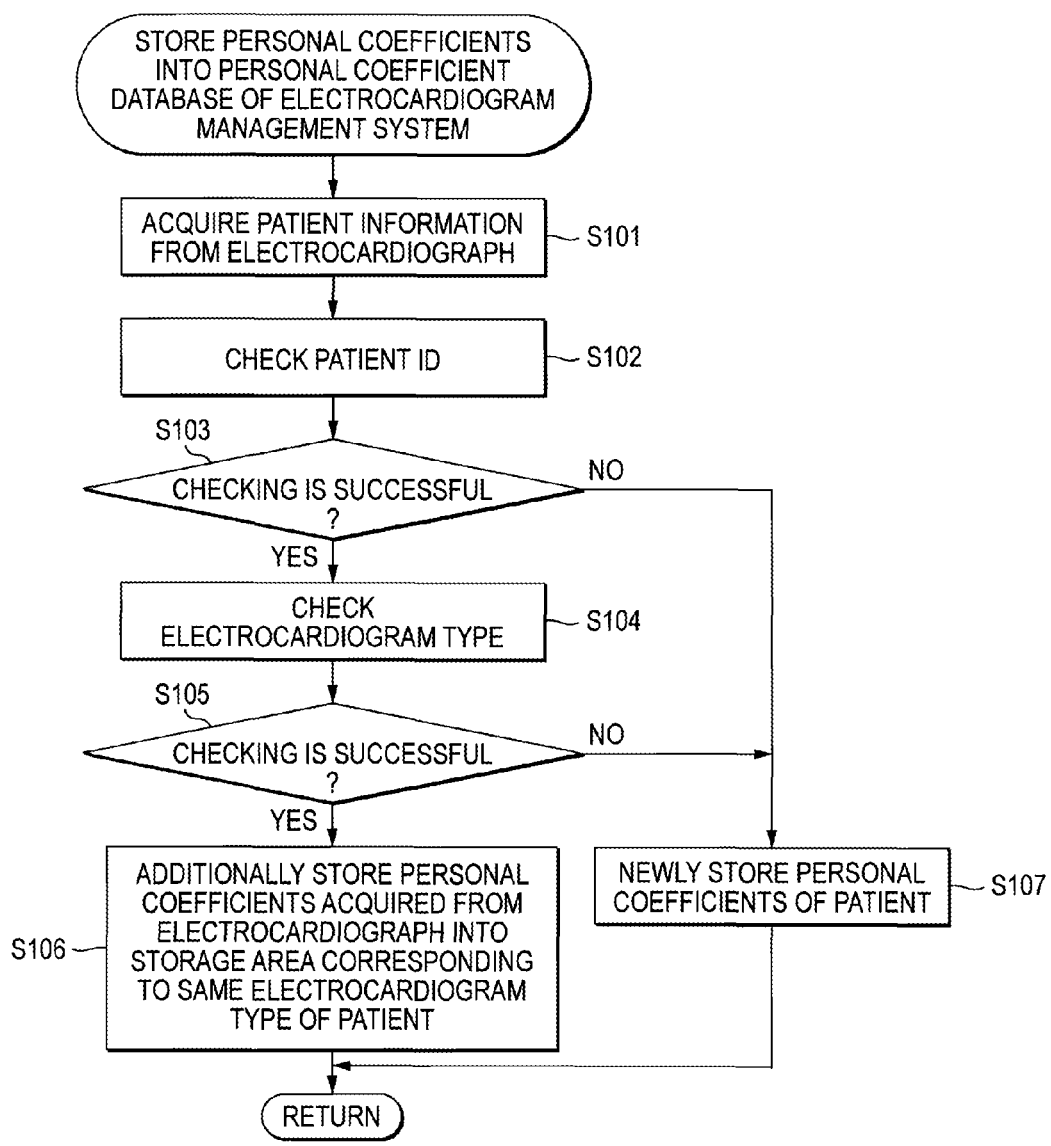
FIG. 15 is a subroutine flow chart showing processing of Step S82 (storing the personal coefficients into the personal coefficient database of the electrocardiogram management system) in the subroutine flow chart of FIG. 13.

FIG. 15 is a subroutine flow chart showing processing of Step S82 (storing the personal coefficients into the personal coefficient database of the electrocardiogram management system) in the subroutine flow chart of FIG. 13. The subroutine flow chart is processed by the personal coefficient management portion 147.

First, the personal coefficient management portion 147 of the electrocardiograph management system 140 acquires patient information from the electrocardiograph 110. The patient information includes a patient ID (unique ID and individual ID), a patient name, a patient age, a patient sex, a measured lead number, measured lead names, a derived lead number, and derived lead names (Step S101). The personal coefficient management portion 147 checks the patient ID with patient IDs stored in the patient information storage portion 142 (Step S102). When a consistent patient ID is present in the patient information storage portion 142, checking is successful (YES in Step S103). In this case, the personal coefficient management portion 147 checks derived electrocardiogram types of personal coefficients stored in the patient information storage portion 112 (Step S104). When personal coefficients of a consistent derived electrocardiogram are present in the personal coefficient database 143, checking is successful (YES in Step S105). In this case, the personal coefficient management portion 147 additionally stores the personal coefficients into a storage area of the same derived electrocardiogram type of the patient in the personal coefficient database 143. That is, when the same patient has already had personal coefficients of the same derived electrocardiogram type, the newly calculated personal coefficients are additionally stored in time series (Step S106).

On the other hand, when a consistent patient ID is not present in the patient information storage portion 142 so that checking is unsuccessful (NO in Step S103) or when personal coefficients of a consistent derived electrocardiogram type are not present in the personal coefficient database 143 so that checking is unsuccessful (NO in Step S105), the personal coefficient management portion 147 stores the personal coefficients into the personal coefficient database 143 newly (Step S107) because the personal coefficients of the patient are absent in the personal coefficient database 143.

According to the derived electrocardiogram generating system and the derived electrocardiogram generating apparatus according to the embodiment, as described above, personal coefficients specific to a patient for obtaining a derived electrocardiogram which is the most suitable for diagnosing heart disease of the patient are used so that the diagnostic accuracy can be improved.

Although the embodiment has shown the exemplary case where personal coefficients are stored in time series on a basis of each patient and each derived electrocardiogram type, personal coefficients do not have to be stored in time series but only the latest personal coefficients may be updated and stored when the storage capacity of the electrocardiograph is small. In addition, in the embodiment, personal coefficients of a specific patient can be used as long as the personal coefficients are present even if the personal coefficients were obtained, for example, two or three years ago. However, in order to make it possible to diagnose heart disease of the patient with high accuracy, it is desirable to generate a derived electrocardiogram using personal coefficients acquired as recently as possible. Accordingly, a period of validity for use (for example, one year since acquisition date) may be set for the personal coefficients. When the personal coefficients expire, acquisition of personal coefficients may be prompted to carry out processing as shown in FIG. 12, in the same manner as when personal coefficients are absent.

In addition, in the embodiment, conversion of an individual ID is performed for retrieving or acquiring personal coefficients between hospitals. Conversion of the individual ID is performed using a unique ID. There are various related-art methods as ID conversion methods. The invention does not have to be limited to the ID conversion method shown in the embodiment, but various related-art methods may be used. For example, open software such as OpenPIXPDQ is known as software for converting an ID into another ID between hospitals. ID conversion may be performed using such open software.

The configuration of the derived electrocardiogram generating system according to the embodiment shown in FIGS. 1 to 4 is a mode for carrying out the invention. The invention is not limited to the mode. Any mode in which personal coefficients specific to a patient and population coefficients are provided and the personal coefficients are used to generate an electrocardiogram when the personal coefficients specific to the patient are present while the population coefficients are used to generate an electrocardiogram when the personal coefficients specific to the patient are not present is included within the technical scope of the invention.

According to an aspect of the invention, a derived electrocardiogram generating system includes a personal coefficient database, a population coefficient database and an electrocardiograph control portion. Personal coefficients specific to a subject, which coefficients are acquired from the subject in advance, are stored in the personal coefficient database so that a derived electrocardiogram of portions effective in diagnosing heart disease of the subject can be generated. Population coefficients which are average values of a plurality of conversion coefficients acquired from an unspecified large number of persons belonging to a statistically significant population are stored in the population coefficient database so that a standard derived electrocardiogram of the subject can be generated.

The electrocardiograph control portion finds whether the personal coefficients specific to the subject are present in the personal coefficient database or not before generating a derived electrocardiogram of the subject. The electrocardiograph control portion generates a higher-accuracy derived electrocardiogram using the personal coefficients by priority when the personal coefficients specific to the subject are present in the personal coefficient database. When the personal coefficients specific to the subject are absent in the personal coefficient database, the electrocardiograph control portion generates a derived electrocardiogram of the subject using the population coefficients in the population coefficient database.

According to an aspect of the invention, a derived electrocardiogram generating method is applied to a derived electrocardiogram generating system including a personal coefficient database storing personal coefficients acquired from a subject and a population coefficient database storing population coefficients which are average values of a plurality of conversion coefficients acquired from an unspecified large number of persons belonging to a statistically significant population.

First, before generating a derived electrocardiogram of the subject, determination is made as to whether there are personal coefficients specific to the subject in the personal coefficient database or not. Next, when the personal coefficients specific to the subject are present in the personal coefficient database, the personal coefficients are acquired from the personal coefficient database. On the other hand, when the personal coefficients specific to the subject are absent in the personal coefficient database, the population coefficients of the subject are acquired from the population coefficient database. Then, the derived electrocardiogram of the subject is generated using the acquired personal coefficients or the acquired population coefficients.

The personal coefficients of the subject are used as coefficients the most suitable to the subject to generate a derived electrocardiogram of desired portions effective in diagnosing heart disease of the subject. On the other hand, the population coefficients are general-purpose coefficients which are average values of a plurality of conversion coefficients acquired from an unspecified large number of persons belonging to a statistically significant population.

Thus, the deriving accuracy can be improved by use of the personal coefficients as compared with that obtained by use of the average general-purpose population coefficients, so that the diagnostic accuracy of the heart disease of the subject can be improved.

According to an aspect of the invention, a derived electrocardiogram of desired portions effective in diagnosing heart disease of a subject can be obtained with high accuracy so that the diagnostic accuracy of the heart disease of the subject can be improved.

What is claimed is:

1. A derived electrocardiogram generating system comprising:
    a personal coefficient database which stores personal coefficients specific to a subject, the personal coefficients being acquired from the subject;
    a population coefficient database which stores population coefficients which are average values of conversion coefficients acquired from an unspecified large number of persons belonging to a statistically significant population; and
    an electrocardiograph control portion:
        which generates a derived electrocardiogram of the subject using the personal coefficients when the personal coefficients are present in the personal coefficient database; and
        which generates a derived electrocardiogram of the subject using the population coefficients when the personal coefficients are absent in the personal coefficient database.

2. The derived electrocardiogram generating system according to claim 1, further comprising:
    a plurality of electrocardiographically measuring electrodes which are adapted to be attached to desired measurement portions of a body surface of the subject to acquire electrocardiographic signals,
    wherein the electrocardiograph control portion calculates the personal coefficients of the subject from the acquired electrocardiographic signals, and stores the calculated personal coefficients in the personal coefficient database.

3. The derived electrocardiogram generating system according to claim 2, wherein the personal coefficients of the subject are stored in the personal coefficient database on a basis of each derived electrocardiogram type.

4. The derived electrocardiogram generating system according claim 1, wherein the electrocardiograph control portion displays a message prompting creation of the personal coefficients when the personal coefficients of the subject are absent in the personal coefficient database.

5. The derived electrocardiogram generating system according to claim 1, further comprising:
    an electrocardiograph which generates the derived electrocardiogram of the subject; and
    an electrocardiogram management system which manages information about the derived electrocardiogram held by the electrocardiograph, wherein
    the personal coefficient database is disposed in each of the electrocardiograph and the electrocardiogram management system, and
    the population coefficient database and the electrocardiograph control portion are disposed in the electrocardiograph.

6. The derived electrocardiogram generating system according to claim 5, further comprising:
    a plurality of electrocardiogram management apparatuses each of which includes the electrocardiograph and the electrocardiogram management system, the plurality of electrocardiogram management apparatuses being connected to one another through a connection network.

7. The derived electrocardiogram generating system according to claim 6, wherein
the plurality of electrocardiogram management apparatuses include different kinds of electrocardiogram management apparatus, and
the electrocardiogram control portion of the electrocardiograph included in one kind of electrocardiogram management apparatus acquires the personal coefficients of the subject from one of the personal coefficient database of the electrocardiograph included in this kind of electrocardiogram management apparatus, the personal coefficient database of the electrocardiogram management system included in this kind of electrocardiogram management apparatus, and the personal coefficient database of the electrocardiogram management system included in another kind of electrocardiogram management apparatus.

8. The derived electrocardiogram generating system according to claim 7, wherein:
the electrocardiogram control portion of the electrocardiograph included in one kind of electrocardiogram management apparatus retrieves the personal coefficients in turn from the personal coefficient database of the electrocardiograph included in this kind of electrocardiogram management apparatus, the personal coefficient database of the electrocardiogram management system included in this kind of electrocardiogram management apparatus, and the personal coefficient database of the electrocardiogram management system included in another kind of electrocardiogram management apparatus.

9. The derived electrocardiogram generating system according to claim 1, wherein the personal coefficients are stored in time series on a basis of each electrocardiogram type and each subject.

10. The derived electrocardiogram generating system according to claim 1, wherein the population coefficients are stored on a basis of each sex, each age, and each electrocardiogram type.

11. A derived electrocardiogram generating method in a derived electrocardiogram generating system including a personal coefficient database and a population coefficient database, the personal coefficient database storing personal coefficients acquired from a subject, the population coefficient database storing population coefficients which are average values of conversion coefficients acquired from an unspecified large number of persons belonging to a statistically significant population, the method comprising:
determining whether the personal coefficients are present in the personal coefficient database or not;
acquiring the personal coefficients when the personal coefficients are present in the personal coefficient database, and acquiring the population coefficients from the population coefficient database when the personal coefficients are absent in the personal coefficient database; and
generating a derived electrocardiogram of the subject using the acquired personal coefficients or the acquired population coefficients.

12. The derived electrocardiogram generating method according to claim 11, further comprising:
attaching a plurality of electrocardiographically measuring electrodes to desired measurement portions of a body surface of the subject to acquire electrocardiographic signals when the personal coefficients of the subject are absent in the personal coefficient database;
calculating the personal coefficients of the subject from the acquired electrocardiographic signals; and
storing the calculated personal coefficients in the personal coefficient database.

* * * * *